United States Patent
Lagae et al.

(10) Patent No.: US 9,617,149 B2
(45) Date of Patent: Apr. 11, 2017

(54) COMPACT FLUID ANALYSIS DEVICE AND METHOD TO FABRICATE

(71) Applicant: IMEC VZW, Leuven (BE)

(72) Inventors: Liesbet Lagae, Leuven (BE); Peter Peumans, Herfelingen (BE)

(73) Assignee: IMEC VZW, Leuven (BE)

( * ) Notice: Subject to any disclaimer, the term of this patent is extended or adjusted under 35 U.S.C. 154(b) by 0 days.

(21) Appl. No.: 14/567,301

(22) Filed: Dec. 11, 2014

(65) Prior Publication Data

US 2015/0093816 A1     Apr. 2, 2015

Related U.S. Application Data

(63) Continuation of application No. PCT/EP2014/060591, filed on May 22, 2014.

(30) Foreign Application Priority Data

May 22, 2013   (EP) .................................... 13168743

(51) Int. Cl.
*B01L 1/00*      (2006.01)
*B01L 3/00*      (2006.01)
(Continued)

(52) U.S. Cl.
CPC ........ *B81C 1/00539* (2013.01); *A61B 5/1411* (2013.01); *A61B 5/150022* (2013.01);
(Continued)

(58) Field of Classification Search
CPC ............. B01L 3/5027; B01L 3/502715; B01L 2300/0645; B01L 3/50853
See application file for complete search history.

(56) References Cited

U.S. PATENT DOCUMENTS 5,919,712 A  *  7/1999   Herron et al. ................. 436/518
6,123,820 A  *  9/2000   Bergkuist et al. ............. 204/411
(Continued)

FOREIGN PATENT DOCUMENTS

WO       2012054904 A2    4/2012

OTHER PUBLICATIONS

International Search Report and Written Opinion for PCT/EP2014/060591 mailed Sep. 1, 2014.
(Continued)

*Primary Examiner* — Nathan Bowers
(74) *Attorney, Agent, or Firm* — McDonnell Boehnen Hulbert & Berghoff LLP

(57) ABSTRACT

The present disclosure relates to a device for analyzing a fluid sample. In one aspect, the device includes a fluidic substrate that comprises a micro-fluidic component embedded in the fluidic substrate configured to propagate a fluid sample via capillary force through the device and a means for providing a fluid sample connected to the micro-fluidic component. The device also includes a lid attached to the fluidic substrate at least partly covering the fluidic substrate and at least partly closing the micro-fluidic component. The fluidic substrate may be a silicon fluidic substrate and the lid may be a CMOS chip. In another aspect, embodiments of the present disclosure relate to a method for fabricating such a device, and the method may include providing a fluidic substrate, providing a lid, and attaching, through a CMOS compatible bonding process, the fluidic substrate to the lid to close the fluidic substrate at least partly.

18 Claims, 15 Drawing Sheets

(51) Int. Cl.
  *B81C 1/00*     (2006.01)
  *G01N 27/414*   (2006.01)
  *A61B 5/15*     (2006.01)
  *F15C 5/00*     (2006.01)
  *F15C 7/00*     (2006.01)
  *G01N 27/22*    (2006.01)
  *B01L 7/00*     (2006.01)

(52) U.S. Cl.
  CPC .... *A61B 5/15087* (2013.01); *A61B 5/150221* (2013.01); *A61B 5/150274* (2013.01); *A61B 5/150358* (2013.01); *B01L 3/50273* (2013.01); *B01L 3/502707* (2013.01); *B01L 3/502715* (2013.01); *F15C 5/00* (2013.01); *F15C 7/00* (2013.01); *G01N 27/227* (2013.01); *G01N 27/4148* (2013.01); *B01L 7/52* (2013.01); *B01L 2300/046* (2013.01); *B01L 2300/0645* (2013.01); *B01L 2300/0663* (2013.01); *B01L 2300/0681* (2013.01); *B01L 2300/0819* (2013.01); *B01L 2300/0887* (2013.01); *B01L 2300/123* (2013.01); *B01L 2300/1833* (2013.01); *B01L 2400/0406* (2013.01); *B01L 2400/0415* (2013.01); *B01L 2400/0688* (2013.01); *B01L 2400/086* (2013.01); *B81C 1/00238* (2013.01); *Y10T 29/494* (2015.01); *Y10T 436/143333* (2015.01)

(56) References Cited

U.S. PATENT DOCUMENTS

| | | | |
|---|---|---|---|
| 2002/0022261 A1* | 2/2002 | Anderson et al. | 435/287.2 |
| 2007/0172388 A1* | 7/2007 | Padmanabhan et al. | 422/58 |
| 2009/0169427 A1* | 7/2009 | Supriya | B01L 3/502707 422/68.1 |
| 2009/0317302 A1 | 12/2009 | McAvoy et al. | |
| 2013/0189796 A1* | 7/2013 | Kanaley | G01N 33/54366 436/501 |

OTHER PUBLICATIONS

Lee, Hakho et al., "IC/Microfuidic Hybrid System for Magnetic Manipulation of Biological Cells", IEEE Journal of Solid-State Circuits, vol. 41, No. 6, Jun. 6, 2006, pp. 1471-1480.

* cited by examiner

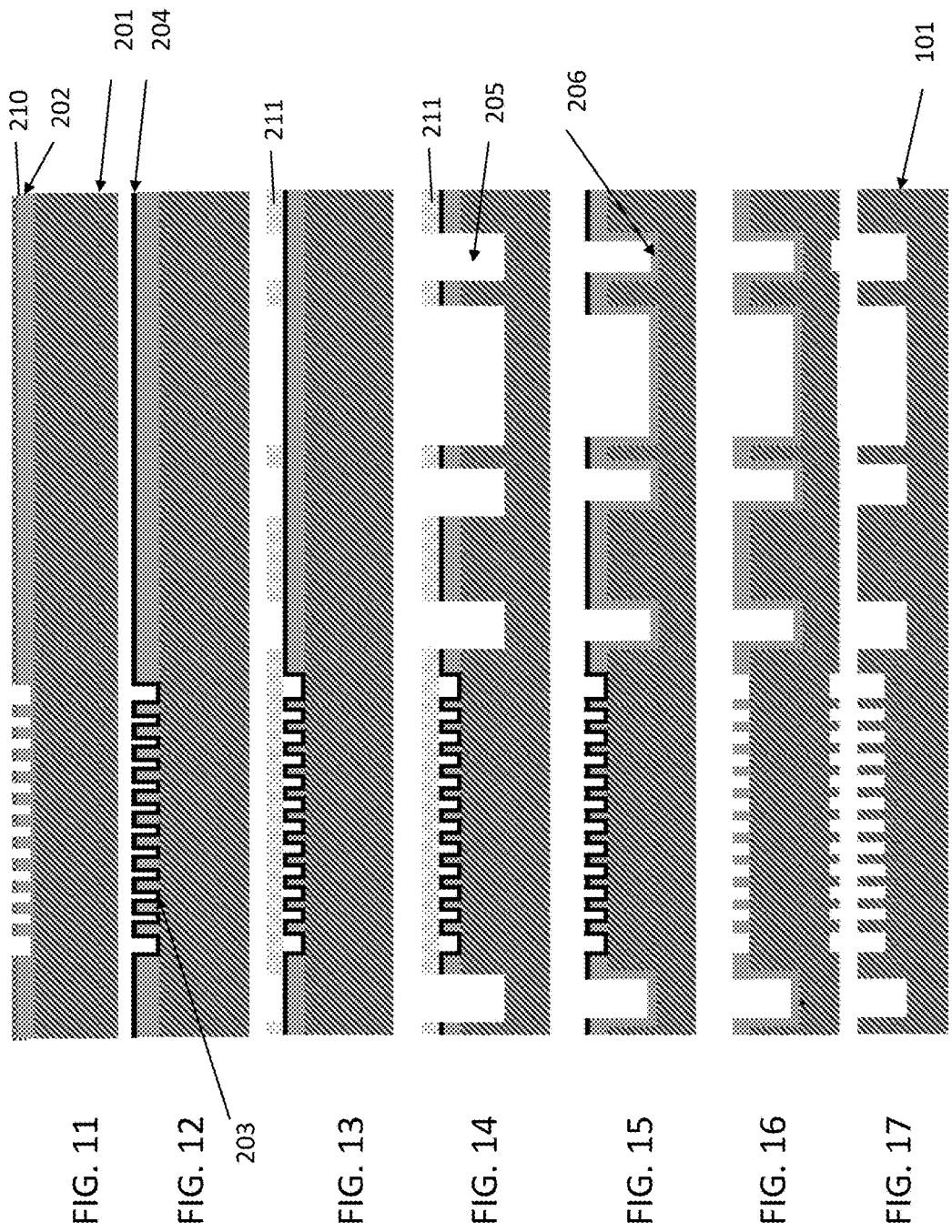

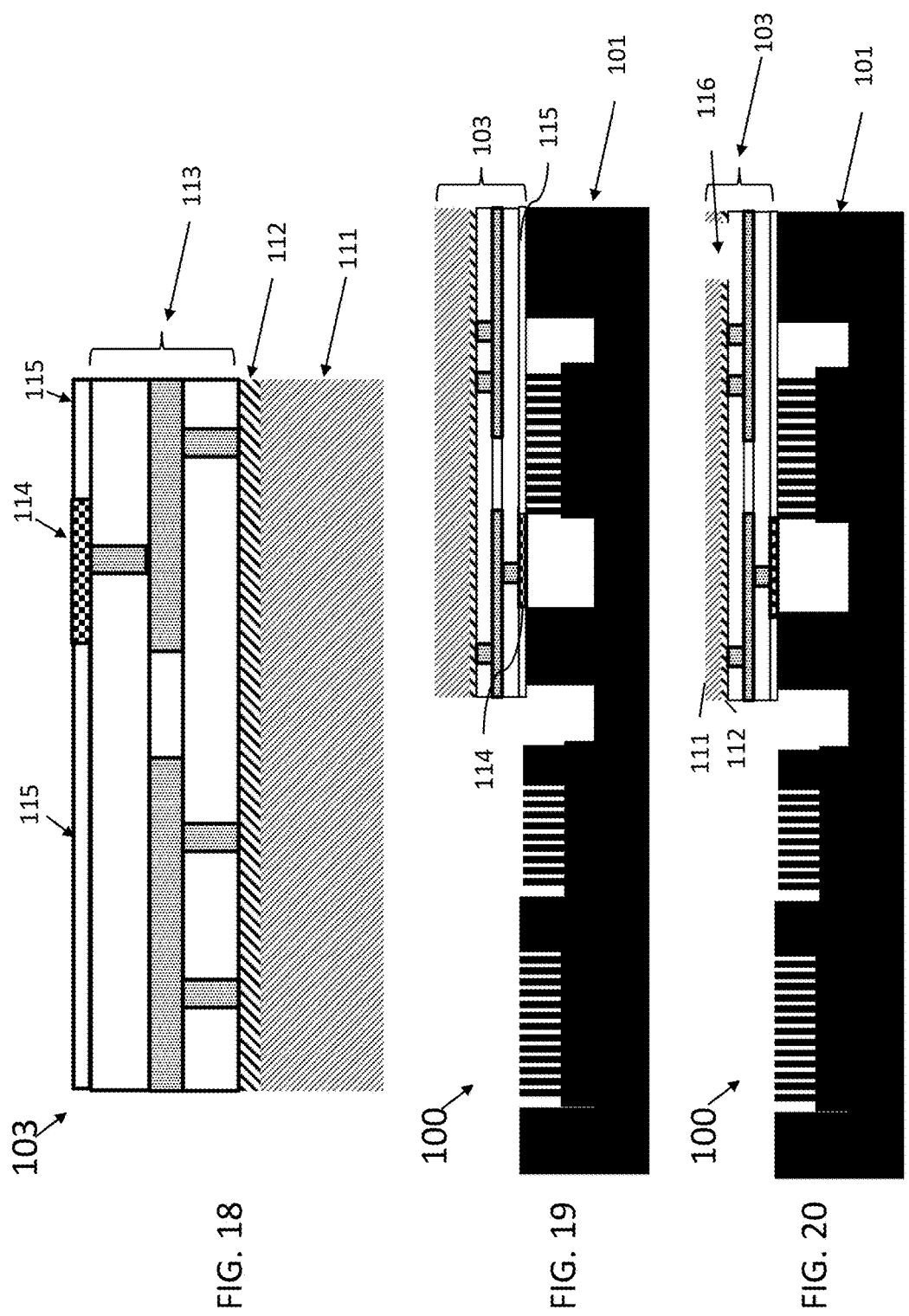

COMPACT FLUID ANALYSIS DEVICE AND METHOD TO FABRICATE

CROSS-REFERENCE TO RELATED APPLICATION

This application is a continuation of International Application No. PCT/EP2014/060591 filed on May 22, 2014, which claims priority to European Patent Application No. 13168743.6 filed on May 22, 2013, the contents of each of which are hereby incorporated by reference.

FIELD OF THE DISCLOSURE

The present disclosure relates to the field of biological analysis devices. In particular, the present disclosure is related to compact devices for the analysis of a fluid sample. More particularly, the present disclosure is related to fully integrated lab-on-a-chip devices for the analysis of fluid samples.

BACKGROUND OF THE DISCLOSURE

Currently, state of the art point-of-care devices for the analysis of blood exist. A disadvantage of these devices is their size which depends on the different components needed to perform blood analyses. In these devices, external pumps are part of the point-of-care device. In some devices, miniature scale pumps are used to propagate a sample through the fluidic channels of the device. The use of pumps increases the size and cost of the device which makes them less suitable for usage as a disposable device. Current disposable devices are typically inserted in expensive readout instruments; with many non-disposable different electronic or optical components to read out the biochemical reactions taking place in the disposable. Another disadvantage of state of the art point-of-care devices is their cost to fabricate.

Other state of the art devices are lateral flow test strips. These test strips are usually fabricated from cellulose which does not allow a precise control of the flow of a fluid sample propagating through the test strips. This narrows the scope of application of these devices.

There is generally a need for a low-cost, easy to use, disposable, and/or compact device for the fully integrated analysis of a fluid sample.

SUMMARY OF THE DISCLOSURE

In a first aspect, the present disclosure relates to a device for analyzing a fluid sample. The device comprises a fluidic substrate, which includes a micro-fluidic component embedded in the fluidic substrate configured to propagate a fluid sample via capillary force through the micro-fluidic component, and a means for providing a fluid sample connected to the micro-fluidic component. The device also includes a lid attached to the fluidic substrate at least partly covering the fluidic substrate and at least partly closing the micro-fluidic component. In one example, the fluidic substrate is a silicon fluidic substrate and the lid is a CMOS chip.

According to embodiments of the present disclosure, at least a part of the lid may be in contact with the fluid sample when the fluid sample is present in the device.

According to embodiments of the present disclosure, the lid may comprise a transistor layer, and the transistor layer may be electrically connected to at least one electrical component. The electrical component may be, for instance, at least one of the following: biosensing circuitry, electrodes for sensing purposes, electrodes for fluid manipulation purposes, circuitry for data communication purposes, circuitry for wireless data communication purposes, temperature sensors, heater electrodes for temperature control, and fluid sensors and electrodes for fluidic viscosity control.

According to embodiments of the present disclosure, the means for providing a fluid sample may be an integrated needle fabricated from silicon and comprising an inner fluidic channel connected to the micro-fluidic component. The needle may be a protruding portion of the fluidic substrate and may be positioned to penetrate skin tissue when pressed against the skin tissue.

According to embodiments of the present disclosure, the fluidic substrate may comprise a cut-out and the needle may be positioned in the cut-out.

According to embodiments of the present disclosure, the fluidic substrate comprises a protection structure for protecting the needle, removably attached to the fluidic substrate.

According to embodiments of the present disclosure, the means for providing a fluid sample may be an inlet. A sample drop may be inserted into the microfluidic component by means of capillary suction. The microfluidic component may comprise different fluidic compartments, for instance for muti-omic analysis. The different microfluidic compartments can have the same or different depths. The different microfluidic compartments may be separated by valves that may be actuated in any suitable way, for instance by fluidic forces or by electricity. Electrodes for actuation may be contained on the fluidic substrate or on the lid.

According to embodiments of the present disclosure, the fluidic substrate or the lid may further comprise at least one optical waveguide to allow optical excitation and sensing of the fluid sample when present in the device. The fluidic substrate or the lid may also comprise filters for rejecting optical excitation from emission to measure a fluorescent signal. The fluidic substrate or the lid may comprise multispectral filters for measuring fluorescent signals with multiple colors. The fluidic substrate or the lid may comprise an optical waveguide and/or a pinhole to irradiate the sample for performing lens-free microscopy.

According to embodiments of the present disclosure, the fluidic substrate or the lid may comprise at least one through-hole for application of a biochemical reagent to at least one region of the micro-fluidic component or to at least one region of the lid.

According to embodiments of the present disclosure, the lid may be bonded to the fluidic substrate using a lithographically patterned polymer.

According to embodiments of the present disclosure, the device may further comprise metal contacts electrically connected to the lid for read-out of electrical signals generated by the fluid and captured by measurement systems in the lid. According to embodiments of the present disclosure, the lid of the device may further comprise CMOS active pixels for readout of optical signals from the fluid.

According to embodiments of the present disclosure, at least part of the fluidic substrate and/or the lid may be fabricated from a transparent material to allow optical inspection of a fluid sample in the micro-fluidic component.

According to embodiments of the present disclosure, the shape of the device may be configured for insertion into a mobile communication device.

In a second aspect, embodiments of the present disclosure relate to a method for fabricating a device for analyzing a fluid sample. The method comprises providing a fluidic substrate, providing a lid, and attaching the fluidic substrate to the lid to close the fluidic substrate at least partly. In one example, the fluidic substrate is a silicon fluidic substrate and the lid is CMOS chip, and the fluidic substrate is attached to the lid using a CMOS compatible bonding process.

According to embodiments of the present disclosure, providing a fluidic substrate may comprise providing a silicon substrate, providing a mask layer (for instance an oxide mask), patterning the oxide mask so as to create fine structures in the oxide mask, providing a protection layer to protect the oxide mask, patterning coarse structures, etching of the coarse structures, growing oxide for protecting the coarse structures, removing the protection layer and etching the fine structures, and removing the oxide.

According to embodiments of the present disclosure, providing a fluidic substrate may comprise providing a silicon substrate, providing a plurality of masks on top of one another, and using each mask for creating microfluidic structures of different depths.

In accordance with particular embodiments of the present disclosure, providing a fluidic substrate may comprise providing a silicon substrate, providing a first oxide mask, patterning microfluidic structures, etching the substrate to a single depth, providing a second oxide mask, patterning microfluidic structures, etching the substrate to a second depth, and, if required, repeating these steps for creating multiple depths of microfluidic structures.

According to particular embodiments, the fluidic substrate and the lid of a device according to embodiments of the present disclosure may be part of a larger fluidic package, which may be made from different materials like for instance polymers, and which may contain larger fluidic structures, reagents, fluidic and electrical interfaces. An advantage thereof is that such system becomes more cost efficient.

According to embodiments of the present disclosure, surfaces of the fluidic substrate and the lid may be partially or fully coated to modify surface interactions of the substrate with the fluid sample.

In a third aspect, the present disclosure provides the use of a device as described in the first aspect of the present disclosure and its embodiments, to perform microscopy. Microscopy may be implemented by using the lid for detecting lens-free images according to the principles of digital holography.

The use of the device as described may perform multi-omic analysis in which the fluidic substrate is used for performing multiple assays in multiple channels and chambers, and the CMOS lid is used to detect multiple signals from all assays. Those signals can combine multiple DNA, RNA, small molecule, cell signals, and the like from the same analyte.

In particular embodiments, the device is used as a single use disposable device for analysis of a small amount of fluid.

In a fourth aspect, the data from the lid may be sent to a smart device, for instance using a wireless connection. The smart device can be used for processing, visualizing and/or transferring the data.

In embodiments of the present disclosure, the combined data gathered from a single same sample may be used in a software algorithm for calculating a parameter correlating to disease or wellbeing of an individual.

Particular and preferred aspects of the disclosure are set out in the accompanying independent and dependent claims. Features from the dependent claims may be combined with features of the independent claims and with features of other dependent claims as appropriate and not merely as explicitly set out in the claims.

These and other aspects of the disclosure will be apparent from and elucidated with reference to the embodiment(s) described hereinafter.

BRIEF DESCRIPTION OF THE DRAWINGS

FIG. 11 to FIG. 17 illustrate a method to fabricate a fluidic substrate for use in a device according to embodiments of the present disclosure.

FIG. 18 illustrates an embodiment of a CMOS chip for use in a device according to embodiments of the present disclosure.

FIG. 19 illustrates the bonding of a CMOS chip with a fluidic substrate, in accordance with embodiments of the present disclosure.

FIG. 20 illustrates the bonding of a CMOS chip with a fluidic substrate, in accordance with embodiments of the present disclosure, wherein the CMOS chip comprises a silicon I/O interconnect.

Figure 1:
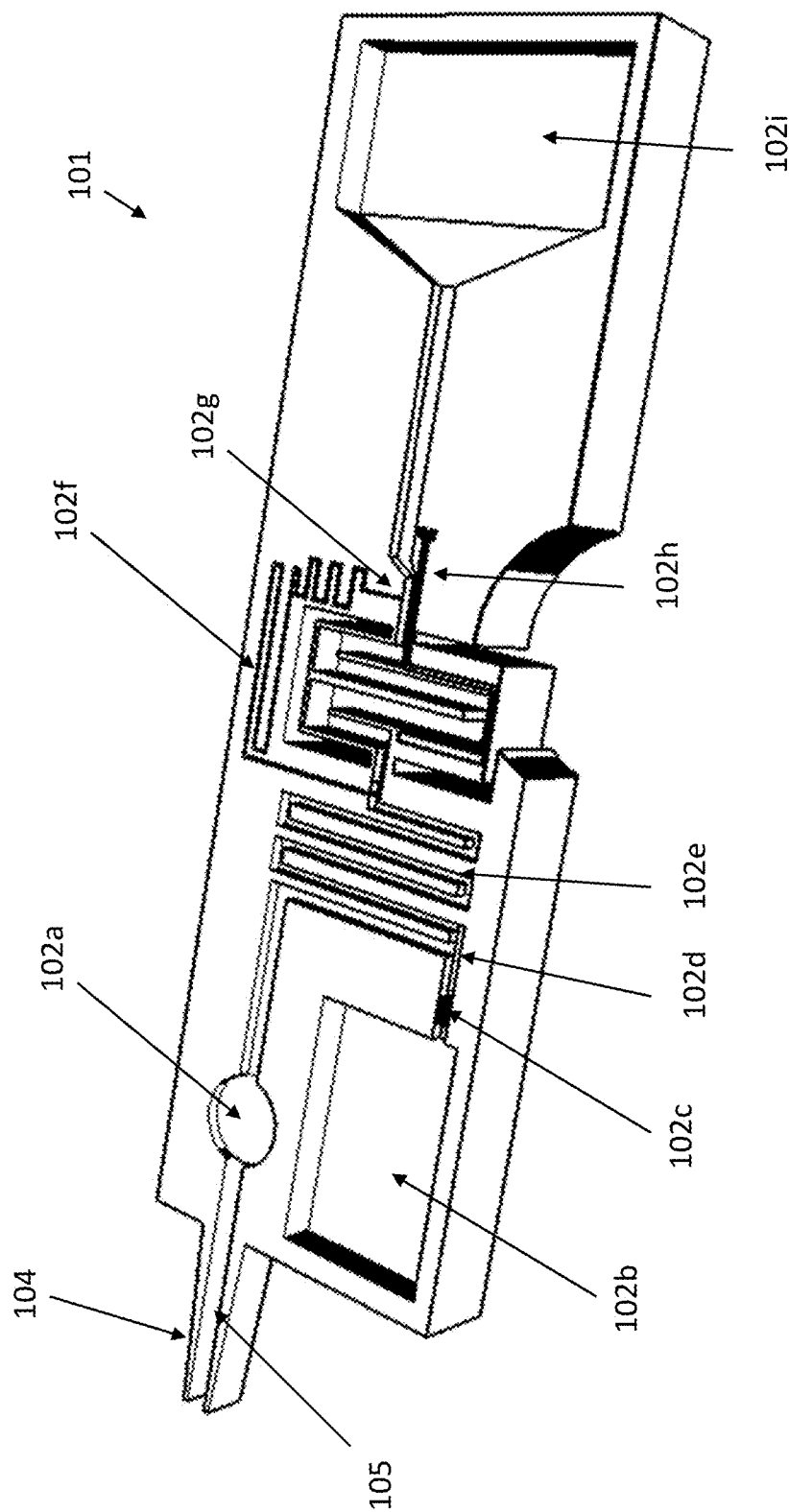
FIG. 1 illustrates a 3D view of an embodiment of a fluidic substrate which may be used in embodiments of the present disclosure.

The drawings are only schematic and are non-limiting. In the drawings, the size of some of the elements may be exaggerated and not drawn on scale for illustrative purposes.

In the different drawings, the same reference signs refer to the same or analogous elements.

DETAILED DESCRIPTION OF THE ILLUSTRATIVE EMBODIMENTS

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions may not correspond to actual reductions to practice of the disclosure.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present disclosure, the only relevant components of the device are A and B.

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of example embodiments of the disclosure, various features of the disclosure are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claims require more features than are expressly recited in each claim. Rather, as the following claims reflect, inventive aspects may lie in less than all features of a single foregoing disclosed embodiment. Thus, the claims following the detailed description are hereby expressly incorporated into this detailed description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

Where in embodiments of the present disclosure reference is made to a "fluid sample", reference is made to any body fluid such as blood, urine, saliva, and the like.

Where in embodiments of the present disclosure reference is made to an "I/O pad" or an "I/O contact", reference is made to a contact such as a metal contact allowing input and/or output of electrical signals of a micro-chip.

Where in embodiments of the present disclosure reference is made to "CMOS", reference is made to a Complementary Metal-Oxide Semiconductor.

Figure 26:
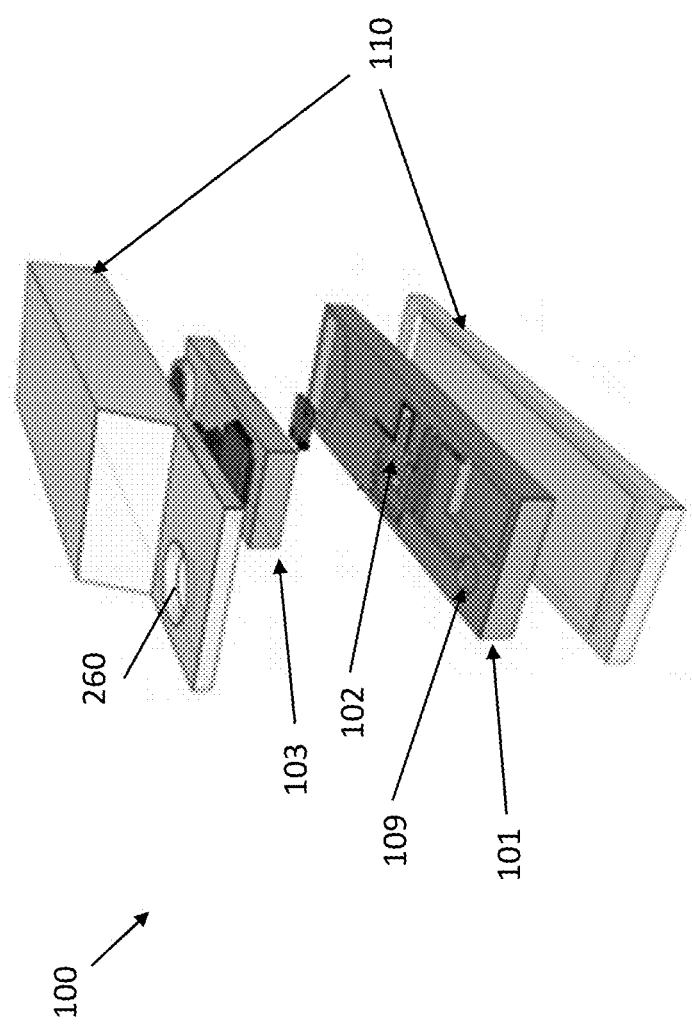
FIG. 26 illustrates a 3D view of a wireless stand-alone device according to an embodiment of the present disclosure.

In a first aspect the present disclosure relates to a device 100 for analyzing a fluid sample, as for instance illustrated in FIG. 26. The device 100 generally includes a fluidic substrate 101 and a lid 103 attached to the fluidic substrate 101 and at least partly covering the substrate 101. The fluidic substrate 101 may comprise a micro-fluidic component 102 (such as illustrated in FIG. 1 by a plurality of microfluidic components including a sample pad 102*a* (e.g., an inlet), a reagent storage 102*b*, a one-time usage hermetic valve 102*c*, a first trigger valve 102*d*, a mixer 102*e*, a delay line 102*f*, a second trigger valve 102*g*, a heater 102*h*, and a wick 102*i*) embedded in the fluidic substrate 101 and configured to propagate a fluid sample via capillary force through the micro-fluidic component 102. The fluidic substrate may also comprise a means for providing a fluid sample connected to the micro-fluidic component 102. The lid 103, by at least partly covering the substrate 101, at least partly closes the micro-fluidic component 102. In embodiments of the present disclosure, the fluidic substrate 101 is a silicon fluidic substrate, and the lid 103 is a CMOS chip.

In embodiments where the fluidic substrate 101 is a silicon substrate and the lid 103 is a CMOS chip, both can be manufactured using mass production compatible silicon process technologies. As an additional advantage, cheap CMOS packaging techniques may be used to bond the silicon substrate to the CMOS chip. This reduces the total cost of the device and allows it to be used as a disposable device and produced in high volume.

FIG. 1 illustrates a 3D view of an embodiment of a fluidic substrate 101.

Figure 3:
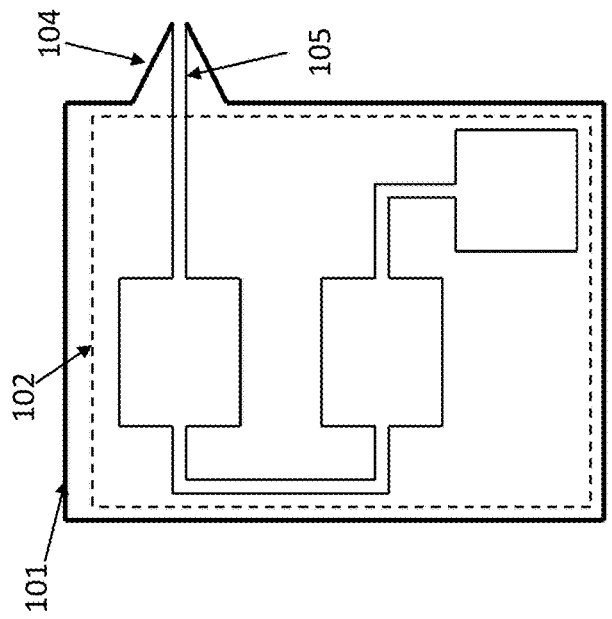
FIG. 3 illustrates a top view of a fluidic substrate used in the device of FIG. 2.
Figure 2:
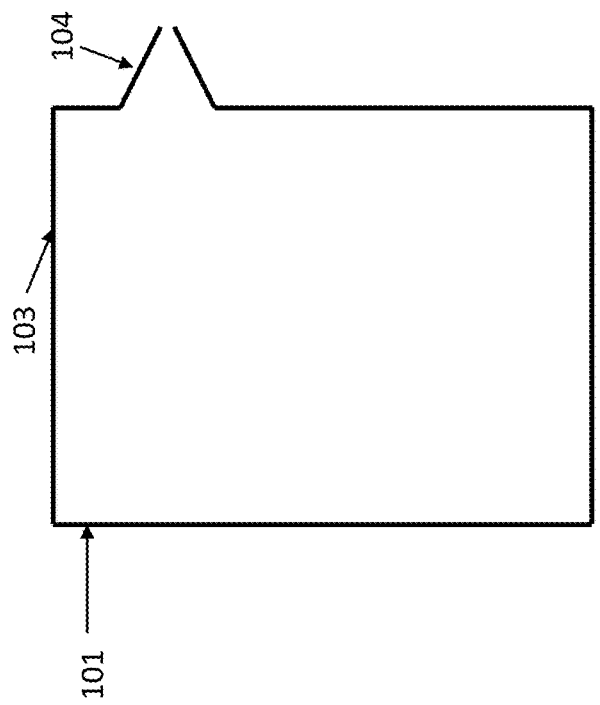
FIG. 2 illustrates a top view of a first embodiment of a device for analyzing a fluid sample according to embodiments of the present disclosure.
Figure 4:
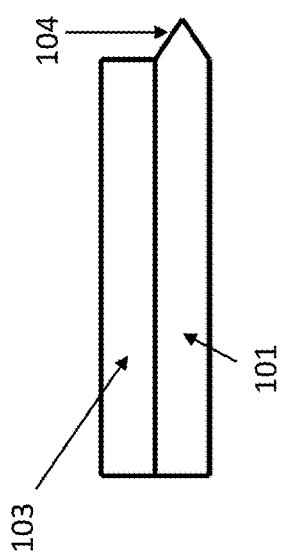
FIG. 4 illustrates a side view of the device of FIG. 2.

A top view of an embodiment of the device 100 is illustrated in FIG. 2, which shows the fluidic substrate 101 and the lid 103 attached to one another. A top view of an example fluidic substrate 101 used in the device of FIG. 2 is illustrated in FIG. 3. A side view of an embodiment of the device 100 of FIG. 2 where the fluidic substrate 101 is attached to the lid 103 is illustrated in FIG. 4.

A device 100 according to embodiments of the present disclosure comprises a fluidic substrate 101 which is attached or bonded to a lid 103. The fluidic substrate 101 comprises a micro-fluidic component 102. The micro-fluidic component 102 may comprise micro-fluidic channels, micro-reactors or other micro-fluidic parts/structures which are interconnected to allow a fluid sample to propagate through the complete micro-fluidic component 102. The micro-fluidic component 102 may comprise a plurality of micro-pillars or microstructures at regular or irregular distances to allow filtering and separation, valving (functioning as a valve), mixing of a fluid sample during capillary flow, among other possible functions.

Figure 27:
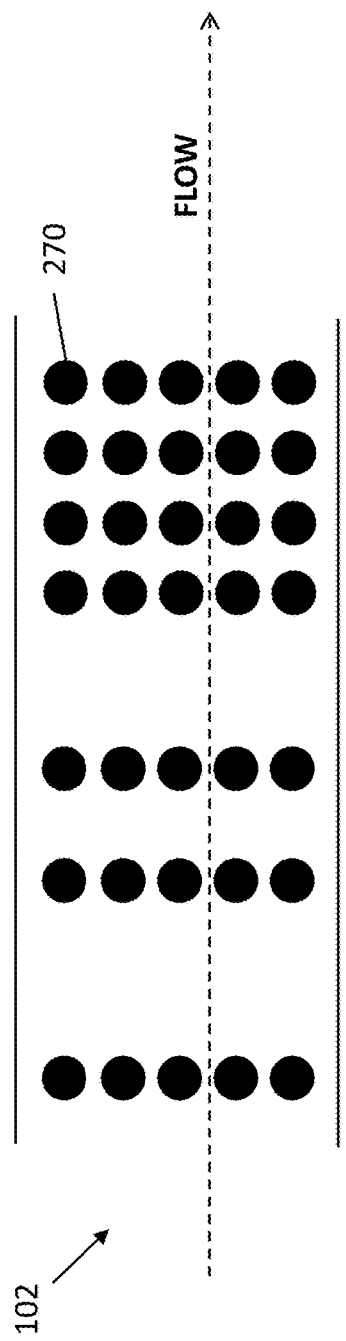
FIG. 27 illustrates a top view of a part of a first embodiment of a micro-fluidic component for use in a device according to embodiments of the present disclosure, the micro-fluidic component comprising micro-pillars.
Figure 28:
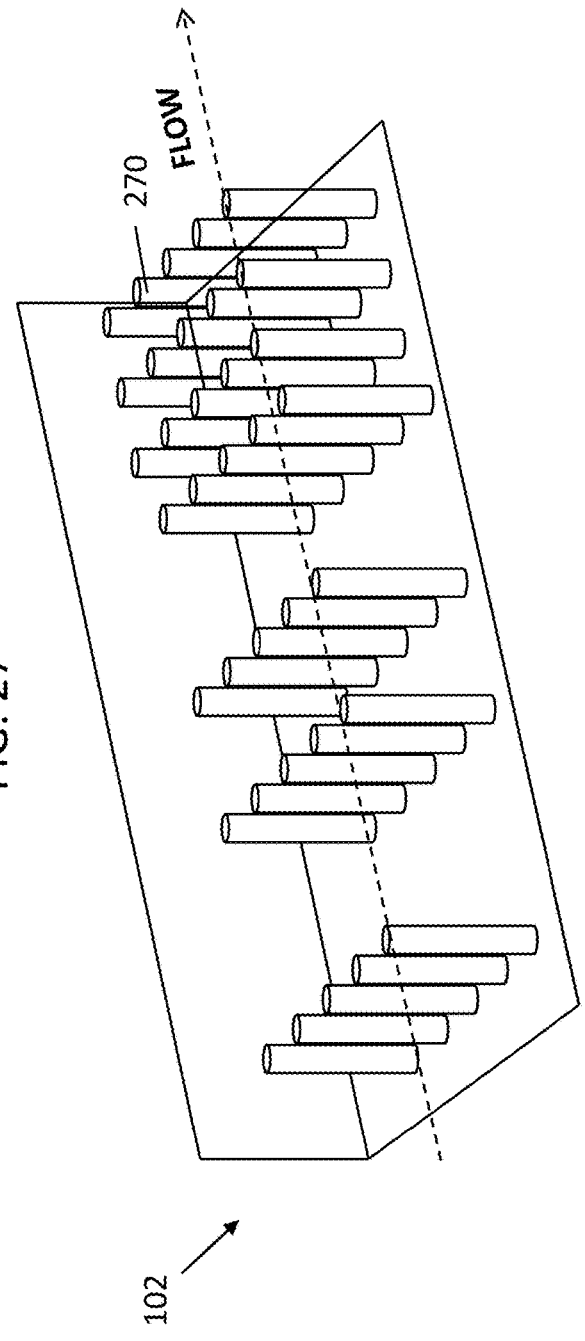
FIG. 28 illustrates a 3D view of a part of the micro-fluidic component of FIG. 27.
Figure 29:
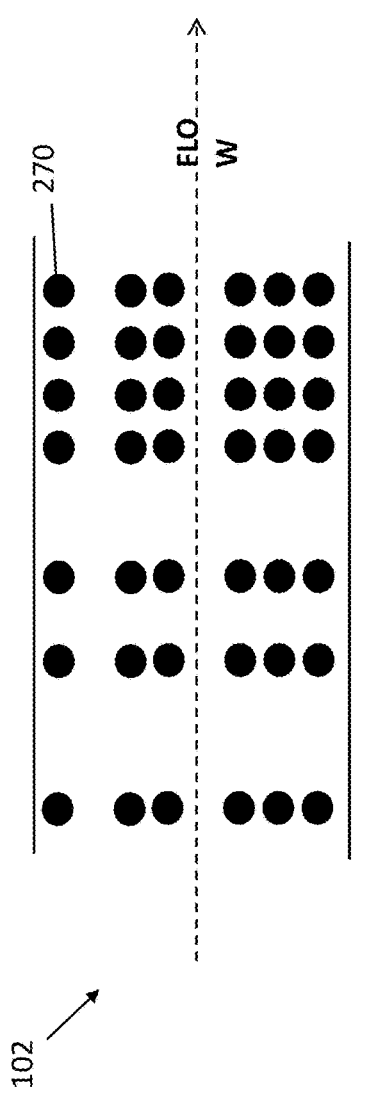
FIG. 29 illustrates a top view of a part of a second embodiment of a micro-fluidic component for use in a device according to embodiments of the present disclosure, the micro-fluidic component comprising micro-pillars.
Figure 30:
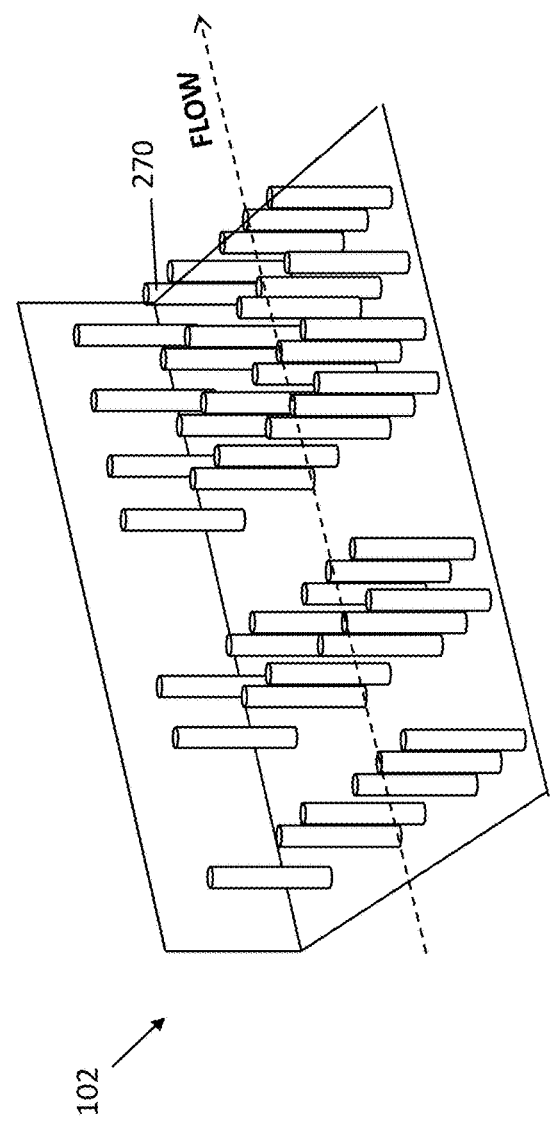
FIG. 30 illustrates a 3D view of a part of the micro-fluidic component of FIG. 29.

FIG. 27 illustrates a top view of a part of an open micro-fluidic component 102 comprising micro-pillars 270 to allow filtering and separation, valving, and mixing of a fluid sample during capillary flow. FIG. 28 illustrates a 3D view of the open micro-fluidic component 102 of FIG. 27 comprising micro-pillars 270. The micro-pillars 270 in FIG. 27 and FIG. 28 are positioned as to form a gradient. This gradient may be advantageous to filter out larger particles in a first part of the micro-fluidic component 102 and to filter out smaller particles in a second part of the micro-fluidic component 102. FIG. 29 and FIG. 30 illustrate another embodiment of a gradient of micro-pillars 270 in the micro-fluidic component 102. The micro-fluidic component 102 may be configured to create a capillary action to propagate a fluid sample through the device 100. The dimensions of the micro-fluidic component 102 may be adapted to create a capillary action in the micro-fluidic component 102 when a fluid sample is present. For example, dimensions and distances between micro-pillars 270 in the micro-fluidic component 102 may be configured to create a capillary action in the micro-fluidic component 102. As an advantage, in embodiments of the present disclosure, the device 100 does not need additional active components (e.g. an active pump) to propagate a fluid sample through the device 100. Thus, the complexity of the device 100 may be reduced compared to other implementations, which reduces fabrication cost and power consumption. Accordingly, as the fabrication costs are low, the device may be used as a disposable fluid analysis device.

It is an advantage of embodiments of the present disclosure that precise control over the flow of a fluid sample in the micro-fluidic component 102 may be achieved by, for example, correctly dimensioning the micro-fluidic channels and/or micro-pillar sizes and distances which are present in the micro-fluidic component 102. Lithographic patterning may be used to fabricate the micro-fluidic component 102 in the fluidic substrate 101. It is an advantage that the lithographic patterning of micro-pillars and micro-fluidic channels of the micro-fluidic component 102 facilitates the accurate control of the dimensions, size and shape of the micro-pillars and micro-fluidic channels, thereby precisely controlling the capillary flow. This precise control over the dimensions, achievable via lithographic processes presents an advantage in achieving more reproducible lateral flow than state of the art lateral flow test strips that are made from porous paper with uncontrolled lateral flow. By varying the dimensions over the length of the device it is possible to slow down and/or to increase the speed of the flow of a fluid sample where desired. This allows implementation of more complex biochemical reactions than the simple flow used in existing lateral flow immunoassay tests. The combination with the functions implemented in the CMOS chip bonded as a lid onto the fluidic substrate 101 further adds temperature control, electrical fluid actuation and valving, integrated biosensing and read out where needed. Therefore, it becomes possible to implement complex assays, including DNA/RNA assays, proteins, small molecules and cells and combinations thereof in one integrated capillary system starting from body fluids. Moreover, the implementation of capillary flow in silicon with controlled lateral flow and with control over the temperature and flow rate results in more accurate point-of-care test results.

In embodiments of the present disclosure, the fluidic substrate 101 comprises a means for providing a fluid sample which is connected to the micro-fluidic component 102.

Figure 25:
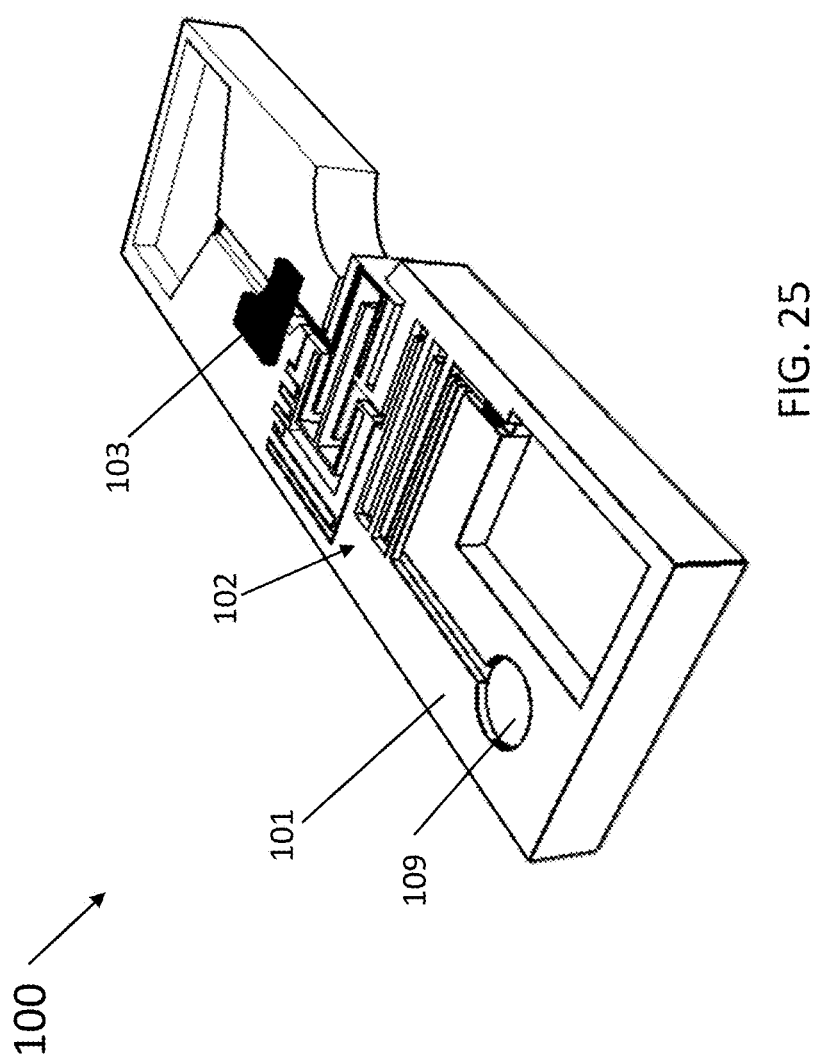
FIG. 25 illustrates a 3D view of a device according to an embodiment of the present disclosure.

The lid 103 functions as a cover for the fluidic substrate 101, wherein the lid 103 fully or partly closes the micro-fluidic component 102. FIG. 25 illustrates an embodiment of the present disclosure wherein the lid 103 partly covers the fluidic substrate 101. The micro-fluidic component 102 may be an open micro-fluidic component 102 in the fluidic substrate 101. According to alternative embodiments of the present disclosure, the dimensions of the lid 103 may be identical to the dimensions of the fluidic substrate 101. The lid 103 may fully or also partially cover the fluidic substrate 101. When the means for providing a fluid sample is an inlet 109 (as illustrated in FIG. 26), for instance a sample pad 102a, the lid 103 may partially cover the fluidic substrate 101, allowing a user to access the inlet 109 to deposit a fluid sample.

According to embodiments of the present disclosure, the device 100 may further comprise one or more electrodes which are placed on the micro-fluidic component 102 of the fluidic substrate 101. These electrodes may be biocompatible electrodes. The electrodes may be electrically connected to the lid 103 and are allowed to interact with a fluid sample in the micro-fluidic component 102 of the device 100 as they may be in direct contact with a fluid sample in the micro-fluidic component 102. While the lid 103 itself may comprise electrodes, it may be advantageous to separate the electrodes from the lid 103 to allow the lid 103 to be smaller, which may, in turn, reduce costs.

According to embodiments of the present disclosure, the micro-fluidic component 102 may comprise a capillary pump.

According to embodiments of the present disclosure, the means for providing a fluid sample may be an integrated needle 104, for instance fabricated from silicon, and comprising an inner fluidic channel 105 connected to the micro-fluidic component 102. The needle 104 may be a protruding portion of the fluidic substrate 101 and may be positioned so as to penetrate skin tissue when pressed against that skin tissue.

The fluidic substrate 101 and the needle 104 may be fabricated from a single piece of silicon. This simplifies the fabrication of the device 100 according to embodiments of the present disclosure, as separate steps to attach a needle 104 to the fluidic substrate 101 are not required. Also, standard CMOS processing techniques may be used to fabricate the needle 104. Preferably the needle 104 is a sharp needle which allows skin tissue to be penetrated. The fluidic substrate 101 and the needle 104 may be both fabricated from silicon. As an advantage, the strength of the silicon allows the needle 104 to be very sharp which eases the penetration of the needle 104 in skin tissue. Further, the strength of the silicon allows skin tissue to be firmly pressed against the needle 104, allowing penetration of skin tissue without bending or breaking the needle 104.

According to embodiments of the present disclosure, the needle 104 may be positioned in a horizontal plane of the fluidic substrate 101, wherein the needle 104 is positioned on a sidewall of the fluidic substrate 101. The needle 104 may be a protruding portion of a sidewall of the fluidic substrate 101. According to a different embodiment, the needle 104 may be positioned on a horizontal plane of the fluidic substrate 101, wherein the needle is positioned perpendicular on a major surface of the fluidic substrate 101. According to embodiments of the present disclosure, the needle 104 may feature an open channel connected to the micro-fluidic component 102, wherein, in use, the skin tissue functions as a side-wall of the needle 104 when skin tissue is penetrated.

The device 100 according to embodiments of the present disclosure may be used by pressing skin tissue of a user against the needle 104. When sufficient force is used, the needle 104 penetrates the skin tissue, allowing blood to enter the inner fluidic channel 105 of the needle 104. The needle 104 comprises a tip which is open to allow a fluid sample to enter the inner fluidic channel 105. When the needle is sharp with a small outer diameter (such as smaller than 200 um) the penetration of the skin tissue will not cause any discomfort to the user. As the inner fluidic channel 105 of the needle 104 is connected to the micro-fluidic component 102 of the fluidic substrate 101, blood may enter the micro-fluidic component 102. Due to capillary force, blood will propagate through the micro-fluidic component 102.

FIG. 1 illustrates an embodiment of the fluidic substrate 101 with an integrated needle 104 (as part of the fluidic substrate 101), the needle having an inner fluidic channel 105 connected to a micro-fluidic component 102. The micro-fluidic component 102 may comprise, for example, a sample pad 102a (an inlet), a reagent storage 102b, a one-time usage hermetic valve 102c, a first trigger valve 102d, a mixer 102e, a delay line 102f, a second trigger valve 102g, a heater 102h, and a wick 102i. As illustrated in FIG. 1, all fluidic components in the fluidic substrate 101 are open. The lid 103 may function as a cover to close some or all fluidic components.

According to embodiments of the present disclosure, the fluidic substrate 101 may comprise a cut-out 106 wherein the needle 104 is positioned in the cut-out 106. The cut-out 106 is a removed part of the fluidic substrate 101 to offer mechanical protection for the needle 104 which resides in the cut-out 106.

Figure 6:
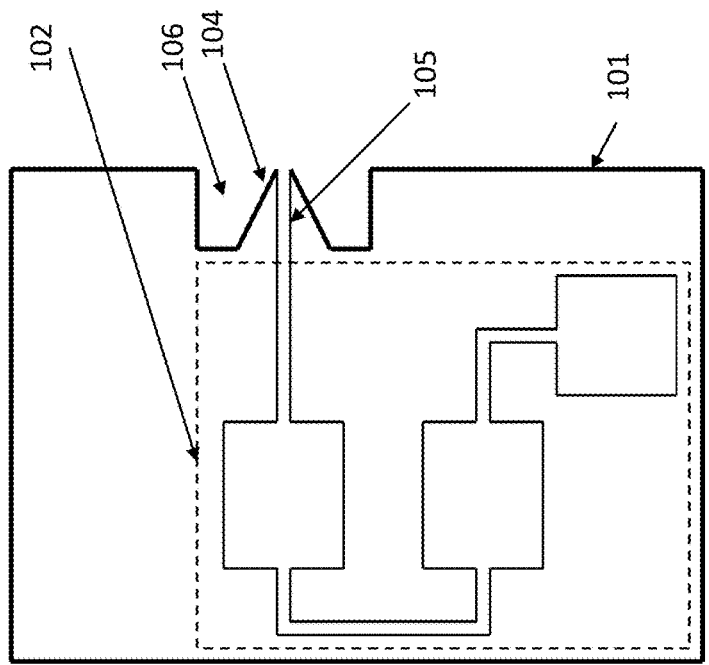
FIG. 6 illustrates a top view of an embodiment of a fluidic substrate featuring a cut-out for a needle, for use in the device of FIG. 5.
Figure 5:
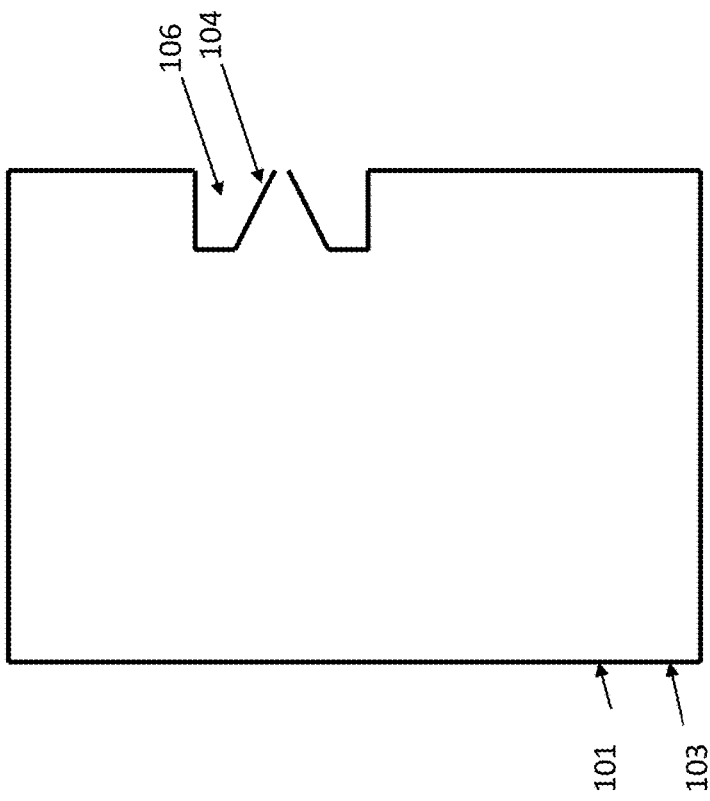
FIG. 5 illustrates a top view of a second embodiment of a device for analyzing a fluid sample according to embodiments of the present disclosure, featuring a cut-out for a needle.
Figure 7:
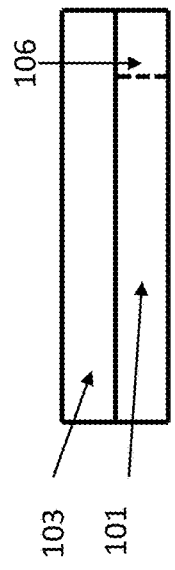
FIG. 7 illustrates a side view of the device of FIG. 5.

FIG. 5 illustrates a top view of an embodiment of the present disclosure wherein the lid 103 is bonded to the fluidic substrate 101. FIG. 6 illustrates a top view of an example fluidic substrate 101 of an embodiment of the present disclosure. FIG. 7 illustrates a side view of an embodiment of the present disclosure wherein the lid 103 is bonded to the fluidic substrate 101.

As illustrated in FIGS. 5, 6, and 7, the needle 104 is located in a cut-out 106 of the fluidic substrate 101. The cut-out 106 protects the needle 104 from breaking, such as when the device 100 is inserted in a slot of an external device (e.g. a mobile device such as a smartphone), for instance for readout. The sidewall of the fluidic substrate 101 may feature the cut-out 106. The needle 104 may be positioned in the cut-out 106 to allow a user to penetrate skin tissue when pressed firmly against the cut-out 106. As a further advantage, during fabrication, the needle 104 may be fabricated while fabricating the cut-out 106. As a result, less material is wasted as only the material for the cut-out 106, excluding the material for the needle 104, needs to be removed. The cut-out 106 and needle 104 may be fabricated using standard silicon processing techniques.

Figure 9:
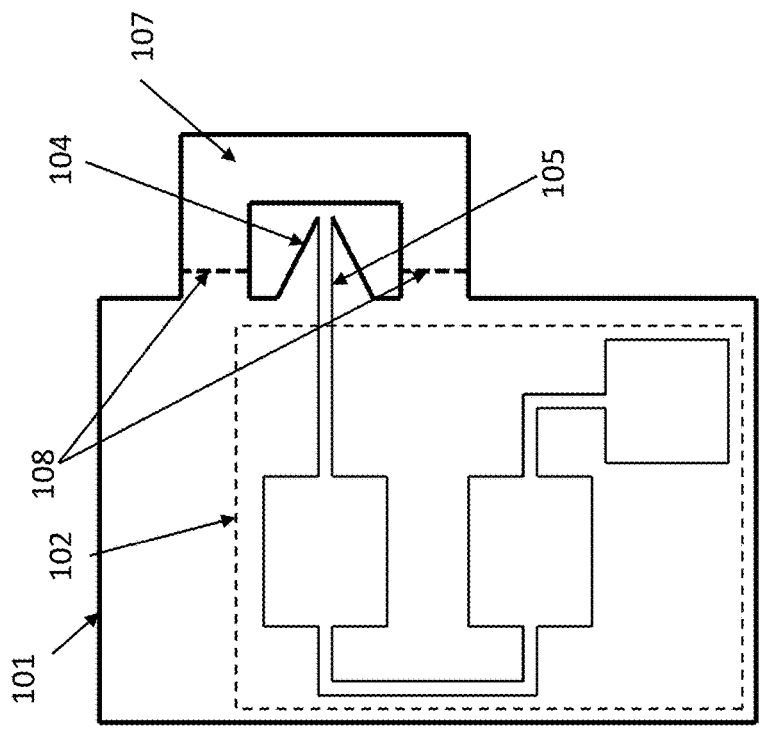
FIG. 9 illustrates a top view of an embodiment of a fluidic substrate featuring a protection structure for a needle, for use in the device of FIG. 8.
Figure 8:
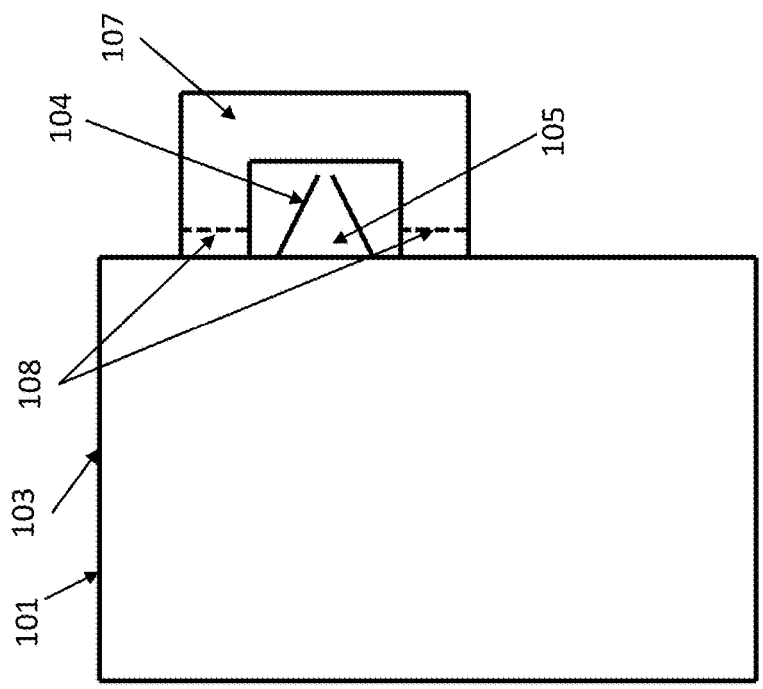
FIG. 8 illustrates a top view of a third embodiment of a device for analyzing a fluid sample according to embodiments of the present disclosure, featuring a protection structure for a needle.
Figure 10:
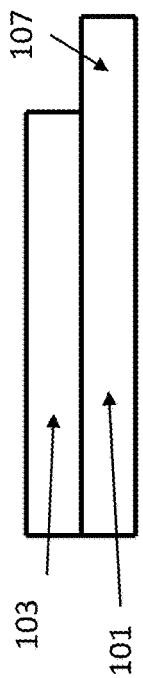
FIG. 10 illustrates a side view of the device of FIG. 8

According to embodiments of the present disclosure, the fluidic substrate 101 may comprise a protection structure 107 for protecting the needle 104, and removably attached to the fluidic substrate 101. According to embodiments of the present disclosure, the protection structure 107 may be attached to the fluidic substrate 101 via at least one anchoring mechanism 108. The protection structure 107 may be detached by breaking the at least one anchoring mechanism 108. The protection structure 107 may be part of the fluidic substrate 101, wherein the anchoring mechanism 108 is a groove in the fluidic substrate 101 to allow breaking of the protection structure 107 at the groove. FIG. 8 is a top view of such an embodiment of a device 100. As can be seen in FIG. 9 (illustrating a top view of an example embodiment of a fluidic substrate 101 for use in a device according to embodiments of the present disclosure, for instance a device as illustrated in FIG. 8), the protection structure 107 is part of the fluidic substrate 101 and features two anchoring mechanisms 108 which allow detaching of the protection structure 107 from the fluidic substrate 101. FIG. 10 illustrates a side view of the device 100 of FIG. 8.

According to embodiments of the present disclosure, the means for providing a fluid sample may be an inlet 109. The inlet 109 may be an indentation in the fluidic substrate 101 which is connected to the micro-fluidic component 102 by a fluidic channel. To use the device, a user may deposit a drop of bodily fluid, such as blood or saliva, on the inlet 109 of the device. Due to capillary force, the bodily fluid will propagate through the micro-fluidic component 102.

FIG. 26 illustrates a de-assembled device 100 according to embodiments of the present disclosure, comprising a fluidic substrate 101 that includes an inlet 109 and a micro-fluidic component 102, a lid 103, and a package 110. The package 110 may comprise a base and a top which can be assembled together to package the fluidic substrate 101 and the lid 103, thus protecting these from environmental influences such as dust. The package may comprise a through-hole 260 for depositing a fluid sample on an inlet 109 of the fluidic substrate 101. When all parts are assembled, the device 100 may function as a stand-alone wireless device for analyzing a fluid sample.

According to embodiments of the present disclosure, at least a part of the lid 103 may be in contact with the fluid sample when the fluid sample is present in the device 100. As the lid 103 is a CMOS chip, electronic circuitry present on a surface of the chip may be in direct contact with the fluid sample when the lid 103 is functioning as a side-wall of an open micro-fluidic component 102 in the fluidic substrate 101. In this case, the side of the chip comprising electronic circuitry may be bonded to an open micro-fluidic component 102 of the fluidic substrate 101 wherein the electronic circuitry is aligned with parts of the micro-fluidic component 102 where interaction with a fluid sample is desired. As an advantage, this may improve the interaction between the electronic circuitry and the fluid sample.

According to embodiments of the present disclosure, the lid 103 may comprise bonding layers to enable bonding of the lid 103 to the fluidic substrate 101.

According to embodiments of the present disclosure, a first side of the fluidic substrate 101 comprising an open micro-fluidic component 102 may be bonded to a first side of the CMOS chip 103 comprising at least one electrical component.

According to an embodiment, the lid 103 comprises a transistor layer, the transistor layer being electrically connected to at least one electrical component, and the electrical component being at least one of the following: biosensing circuitry, electrodes for sensing purposes, electrodes for fluid manipulation purposes, circuitry for data communication purposes, circuitry for wireless data communication purposes, temperature sensors, heater electrodes for temperature control or temperature cycling, and fluid sensors and electrodes for fluidic viscosity control. The circuitry for wireless data communication may comprise provisions for communication via a Bluetooth radio or a WiFi module for wirelessly transmitting data from electronic circuitry in the lid 103. As an advantage, the device 100 may communicate with an external device such as a mobile device which may be used to further process the data.

According to an embodiment, the lid 103 is a CMOS chip. According to embodiments of the present disclosure, the CMOS chip comprises a silicon substrate 111, a transistor layer 112, at least one electrical component electrically connected to the transistor layer 112, and at least one bonding layer 115. The at least one electrical component may be biosensing circuitry, electrodes for sensing purposes, electrodes for fluid manipulation purposes, circuitry for data communication purposes, circuitry for wireless data communication purposes, temperature sensors, heater electrodes for temperature control, and fluid sensors and electrodes for fluidic viscosity control.

A particular embodiment of a lid 103 according to embodiments of the present disclosure is illustrated in FIG. 18. In this embodiment, the CMOS chip 103 comprises a silicon substrate 111. Atop the silicon substrate 111 a transistor layer 112 may be present. Atop the transistor layer 112 an interconnection layer 113 may be present. Atop the transistor layer 112, at least one electrical component may be present electrically connected to the transistor layer 112 via the interconnection layer 113. The interconnection layer 113 may comprise a plurality of metal layers. According to embodiments of the present disclosure, atop the transistor layer 112, a bonding layer 115 and at least one electrode 114 may be present. The electrode 114 may be electrically connected to the transistor layer via the interconnection layer 113.

According to embodiments of the present disclosure, the at least one electrical component may be a biocompatible electrode which is fluid corrosion free and chemically inert. According to a specific embodiment, the at least one electrode 114 is TiN electrode.

According to embodiments of the present disclosure the bonding layer 115 may be a layer which allows bonding of the CMOS chip 103 to the fluidic substrate 101 at low temperatures and voltages. This is advantageous as these conditions do not damage the CMOS chip, neither do they damage reagents or for instance proteins which may be provided on the microfluidic substrate 101. According to a specific embodiment, the bonding layer 115 may be a SiO2 or polymer layer.

FIG. 19 illustrates a device 100 according to embodiments of the present disclosure, wherein a CMOS chip 103 as illustrated in FIG. 18 is bonded to a fluidic substrate 101. The side of the CMOS chip 103 comprising the bonding layer 115 and the electrode 114 is bonded to the side of the fluidic substrate 101 comprising an open micro-fluidic component 102. This means that the CMOS chip 103 as illustrated in FIG. 18 is flipped upside down with respect to its position as illustrated in FIG. 18. The electrode 114 is thereby in direct contact with a fluid sample present in the micro-fluidic component 102. The bonding layer 115 is used to attach the CMOS chip 103 to the fluidic substrate 101.

According to embodiments of the present disclosure, the CMOS chip 103 may comprise at least one silicon I/O connection 116, as illustrated in FIG. 20. The silicon I/O connection 116 may be a backside opening through the substrate 111 to access electrical signals of the CMOS chip 103 in the transistor layer 112. Further, in yet alternative embodiments, the silicon I/O connection 116 may be a backside opening through both the substrate 111 and the transistor layer 112 to access electrical signals of the CMOS chip 103 in the interconnection layer 113. FIG. 20 illustrates the device 100 wherein a CMOS chip 103 is bonded to a fluidic substrate 101 and wherein the CMOS chip 103 features a silicon I/O connection 116 through both the substrate 111 and the transistor layer 112.

According to embodiments of the present disclosure, the fluidic substrate may comprise an open micro-fluidic component 102 and the fluidic substrate may be covered partly by the CMOS chip 103. It may be advantageous that a part of the micro-fluidic component 102 is not covered as this can allows reagents to be applied/spotted on specific open parts of the micro-fluidic component 102. In this case, no extra through-holes are needed to apply reagents after bonding of the fluidic substrate 101 to the CMOS chip 103. In this example, it is also advantageous that the CMOS chip area is smaller, as the active electronics are the more expensive part of the device.

According to embodiments of the present disclosure, the CMOS chip 103 may further comprise at least one I/O pad 117. The at least one I/O pad 117 may be located on the interconnection layer 113.

Figure 21:
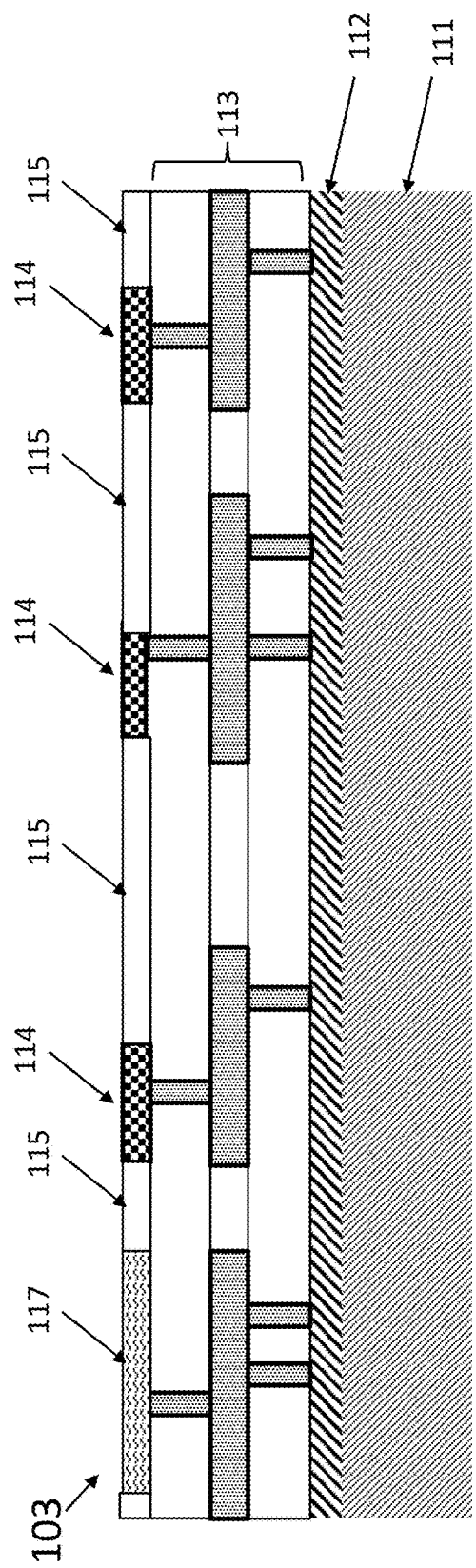
FIG. 21 illustrates an embodiment of a CMOS chip for use in a device according to embodiments of the present disclosure, the CMOS chip comprising an I/O pad.

FIG. 21 illustrates an embodiment of a CMOS chip 103. The CMOS chip 103 comprises a silicon substrate 111. Atop the silicon substrate a transistor layer 112 is present. Atop the transistor layer 112, an interconnection layer 113 is present. The interconnection layer 113 may comprise a plurality of metal layers to interconnect the transistor layer 112 with electrical components. Atop the transistor layer 112, a bonding layer 115, an I/O pad 117 and, in the embodiment illustrated, a plurality of electrodes 114 are present. The electrodes 114 are electrically connected to the transistor layer 112 via the interconnection layer 113. The I/O pad 117 is also electrically connected to the transistor layer 112 via the interconnection layer 113.

According to embodiments of the present disclosure, a first part of a first major surface of the CMOS chip 103 may cover the fluidic substrate 101, and a second part of the first major surface of the CMOS chip 103 may not cover the fluidic substrate 101. In these embodiments, the CMOS chip 103 may either be larger than the fluidic substrate 101, or it may be laterally shifted with respect to the fluidic substrate 101 so that a portion of the CMOS chip 103 forms an overhang with respect to the fluidic substrate 101. The second part of the first major surface of the CMOS chip 103 may comprise at least one I/O pad 117 to have access to the I/O pad 117.

Figure 22:
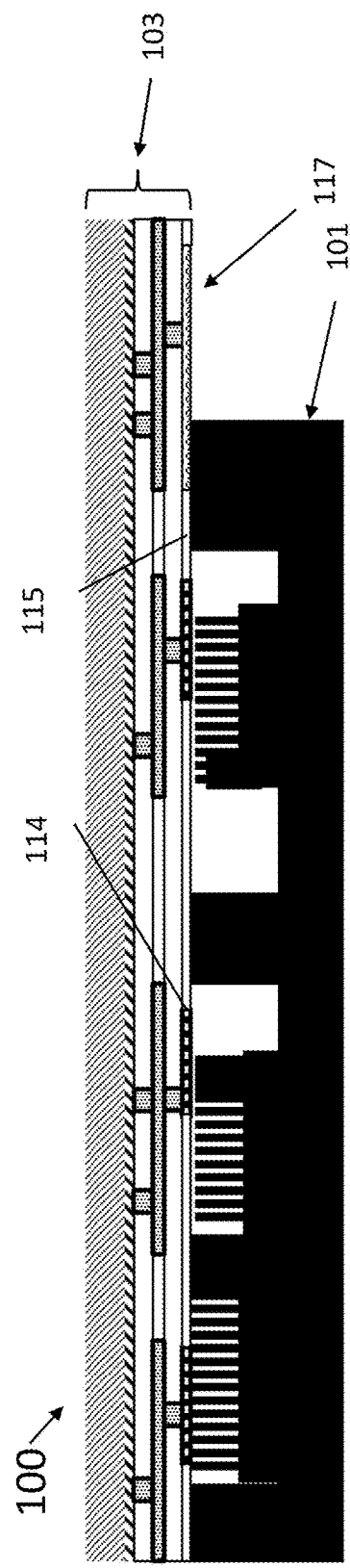
FIG. 22 illustrates an embodiment of a CMOS chip for use in a device according to embodiments of the present disclosure, the CMOS chip comprising an I/O pad bonded to a fluidic substrate, wherein a part of the CMOS chip overlaps the fluidic substrate.

FIG. 22 illustrates a CMOS chip 103 as illustrated in FIG. 21, bonded to a fluidic substrate 101. A first part of the CMOS chip 103 at least partly, and in the embodiment illustrated fully covers the fluidic substrate 101, wherein electrodes 114 are in direct contact with a fluid sample when present in the micro-fluidic component 102 of the device 100. The bonding layers 115 are used to bond a first part of the CMOS chip 103 to the fluidic substrate 101. A second part of the CMOS chip 103 forms an overhang which does not cover the fluidic substrate 101. The second part comprises the I/O pad 117. As an advantage, this overhang allows easy access to the I/O pad 117. This allows standard I/O pad dimensions and packaging approaches to be used for inserting the substrate in slots typically used for smartcards, for example. It is a further advantage that additional processing steps to fabricate silicon I/O connections (e.g. a hole through the substrate and transistor layer) to access electrical signals in the CMOS chip 103 are not required.

According to embodiments of the present disclosure, the fluidic substrate 101 further comprises at least one optical waveguide to allow optical excitation and sensing of the fluid sample when present in the device 100.

According to embodiments of the present disclosure, the fluidic substrate 101 or the lid 103 comprises at least one through-hole for application of a biochemical reagent to a region of the micro-fluidic component 102 or to a region of the lid 103. The through-holes in the fluidic substrate 101 or the lid 103 allow the application of biochemical reagents to specific regions of the micro-fluidic component 102 or to specific regions of the lid 103. This is advantageous as it allows reagents to be applied after attachment of the lid 103 to the fluidic substrate 101.

Figure 23:
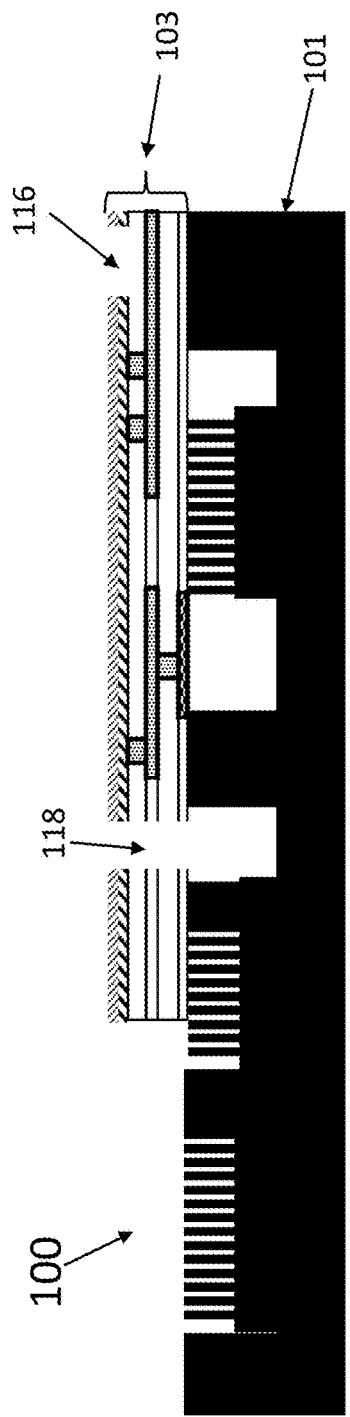
FIG. 23 illustrates the bonding of a CMOS chip with a fluidic substrate, in accordance with embodiments of the present disclosure, wherein the CMOS chip comprises a through hole.

According to embodiments of the present disclosure, the CMOS chip 103 may comprise at least one through-hole 118. When attached to the fluidic substrate 101, the through hole 118 in the CMOS chip 103 allows reagent spotting on a specific location of the micro-fluidic component 102 in the fluidic substrate 101 or on a specific part of the CMOS chip 103. FIG. 23 illustrates such an embodiment wherein the CMOS chip 103 comprises one through-hole 118. In this embodiment, the CMOS chip further comprises a silicon I/O connection 116. As illustrated, the CMOS chip 103 completely covers a part of the fluidic substrate 101.

Figure 24:
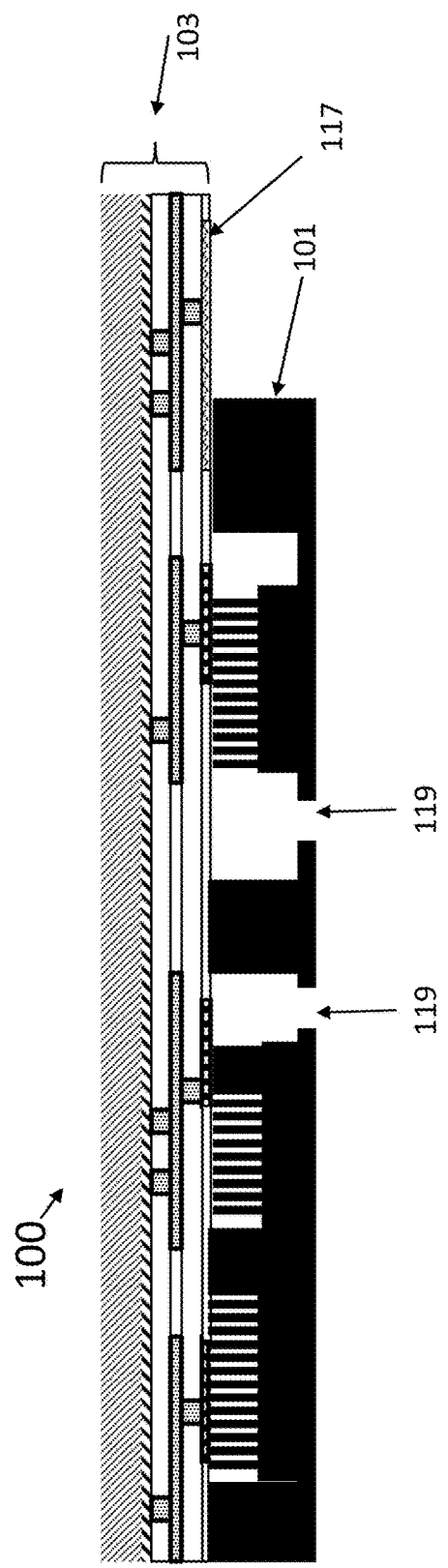
FIG. 24 illustrates the bonding of a CMOS chip with a fluidic substrate, in accordance with embodiments of the present disclosure, wherein the fluidic substrate comprises two through holes.

According to the same or alternative embodiments of the present disclosure, a first side of the fluidic substrate 101 comprises the open micro-fluidic component 102. The other side, opposite to the side where the micro-fluidic component 102 is provided, may comprise a at least one through-hole 119. The through-hole 119 allows reagent spotting on a specific location of the micro-fluidic component 102 in the fluidic substrate 101 or on a specific part of the CMOS chip 103. FIG. 24 illustrates such an embodiment wherein the fluidic substrate comprises two through-holes 119. A part of the CMOS chip 103 covers the fluidic substrate 101, and the part not covering the fluidic substrate 101 but forming an overhang comprises an I/O pad 117.

According to embodiments of the present disclosure, the lid 103 may be bonded to the fluidic substrate 101 using a polymer, which may preferably be a lithographically patterned polymer. The material for forming the bonding between the lid 103 and the fluidic substrate 101 should be suitable for perform a Si—Si bonding, preferably at low temperature, for instance room temperature. This is compatible with CMOS circuits being present on the lid 103 and which should not be destroyed by the bonding process, and with reagents being present on or in the fluidic substrate 101, and which should also not be destroyed by the bonding process. Suitable bonding materials for bonding the lid 103 to the fluidic substrate 101 are for instance photopatternable PDMS, obtainable from Dow Corning; SU8, obtainable from Micro Chem; or OSTE, obtainable from Mercene Labs. These bonding materials all have room temperature as the bonding temperature.

According to another embodiment of the present disclosure, the lid 103 is bonded to fluidic substrate 101 using a CMOS compatible packaging technique. The use of CMOS packaging techniques may be used when the fluidic substrate 101 is a silicon substrate and the lid 103 is a CMOS chip.

According to embodiments of the present disclosure, the device 100 may further comprise metal contacts electrically connected to the lid 103 for read-out of electrical signals from the lid 103. The metal contacts may be located on the lid 103, and may be electrically connected to electronic circuitry in the lid 103. The position and shape of the metal contacts may be selected according to standards to allow insertion of the device in standardized slots, such as slots for memory cards (e.g. CompactFlash, SmartMedia, MultiMedia Card, or Secure Digital (SD) memory cards) commonly used in communication devices such as mobile devices. The insertion of the device 100 in a mobile device allows processing of the electrical signals from the lid 103 by a processor and/or other electronic components present in the mobile device. For example, a processor of a smartphone may be used to process electrical signals and/or to display data.

According to embodiments of the present disclosure, at least a part of the fluidic substrate 101 and/or the lid 103 may be fabricated from a transparent material to allow optical inspection of a fluid sample when the fluid sample is present in the micro-fluidic component 102. The part of the fluidic substrate 101 that is fabricated from a transparent material may be part of the micro-fluidic component 102 of the device 100. The transparent part may be a side-wall of the micro-fluidic component 102 of the device 100. The transparent material allows optical inspection of a fluid sample in the device 100. An optical detector may be used to optically inspect a fluid sample, in order, for instance, to detect an analyte. The optical detector may be an image sensor which may be part of an external device or may be integrated in the device 100. The transparent material may be a transparent oxide or polymer. For microscopy purposes, a part of the lid 103 or a part of the fluidic substrate 101 may be transparent. For lens-free imaging purposes, a part of the lid 103 and a part of the fluidic substrate 101 may be transparent to enable working in transmission mode, wherein a radiation source may be used to radiate an object in a fluid sample in the device 100 through the transparent part of the lid 103 and a detector may be used to detect signals from the radiated object through the transparent part of the fluidic substrate 101. The signals may be diffraction patterns of a radiated object in the fluid sample.

Figure 33:
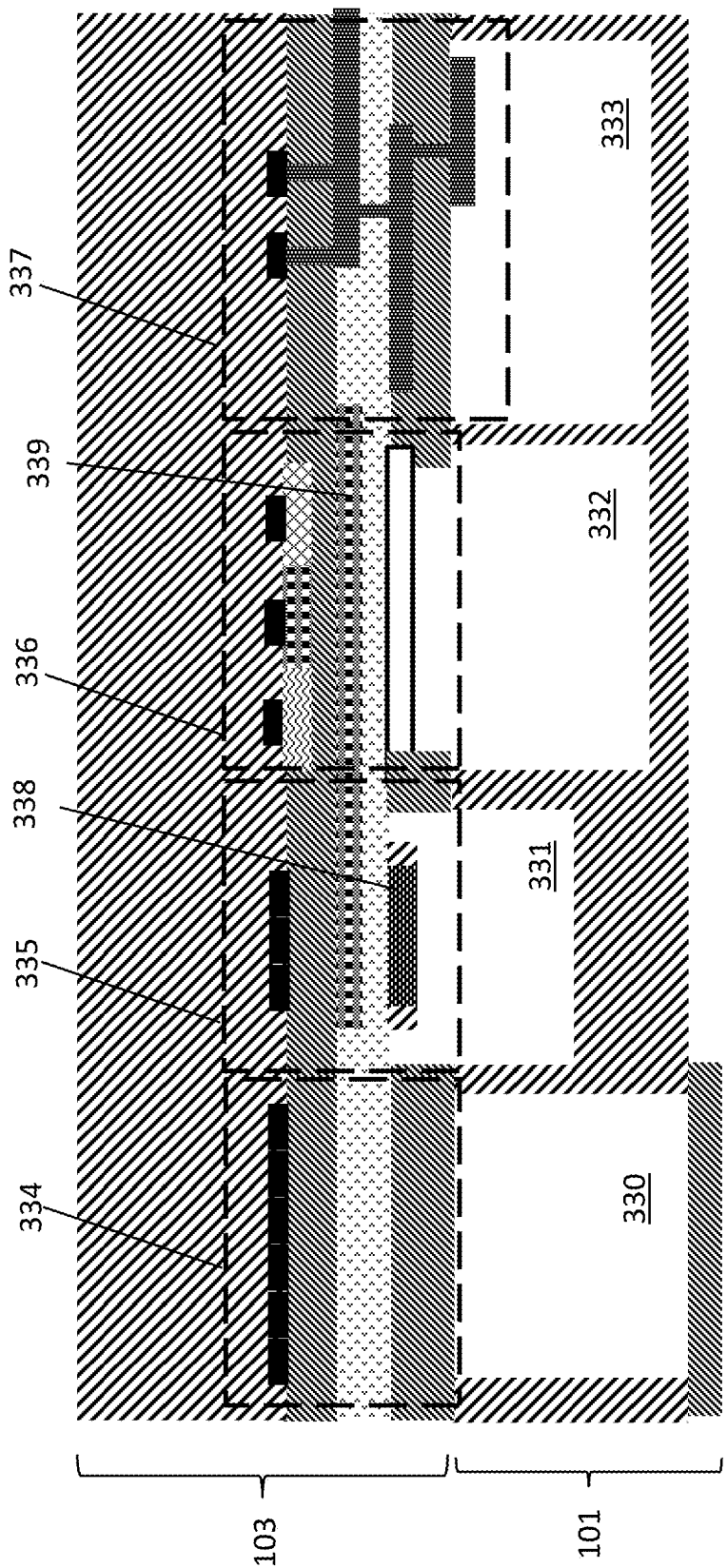
FIG. 33 is a cross-sectional view of a device according to embodiments of the present disclosure, wherein a plurality of functionalities are supported by a single CMOS technology.

FIG. 33 illustrates a device 100 according to embodiments of the present disclosure, where a fluidic substrate 101 and a lid 103 are bonded to one another. The fluidic substrate 101 comprises different microfluidic components for multi-omic analysis, such as a plurality of chambers 330, 331, 332, 333 illustrated in the embodiment of FIG. 33 and microfluidic channels (not illustrated). The chambers may have different depths, depending on their function and the type of measurement being performed. The chambers may be separated by valves that may be actuated in any suitable way, for instance by fluidic forces or by electricity. Electrodes for actuation may be provided on the fluidic substrate 101 or on the lid 103. The CMOS chip forming the lid 103 may thus incorporate different functionalities, such as for instance a CMOS microscopic imager 334, CMOS optical detectors 335, 336, and CMOS electrical circuitry 337 for heating and/or sensing. The CMOS microscopic imager 334 may comprise CMOS active pixels for readout of optical signals from the fluid sample in the microfluidic component 102. The CMOS optical detector 335 may comprise an optical resonator 338. A waveguide 339 may be present for transporting measurement light from one location of the CMOS chip 103 to another location. The waveguide may for instance be used for irradiating the sample for performing lens-free microscopy. Furthermore, filters may be provided in the fluidic substrate 101 or in the lid 103 for rejecting optical excitation from emission, so as to enable measurement of a fluorescent signal. Also multispectral filters may be provided in the fluidic substrate 101 or in the lid, for measurement of fluorescent signals with multiple colors.

In this way, detection of different types of markers can be performed within a single, preferably disposable, detection device according to embodiments of the present disclosure.

According to embodiments of the present disclosure, the shape of the device 100 allows insertion into a mobile communication device. According to embodiments of the present disclosure, the device 100 has the shape/dimensions of a memory card. It is an advantage of embodiments of the present disclosure that the dimensions of the device 100 may be according to standards, e.g., according to standards of memory cards used in mobile devices such as: Compact-Flash, SmartMedia, MultiMedia Card, Secure Digital memory cards, or any other type.

Figure 31:
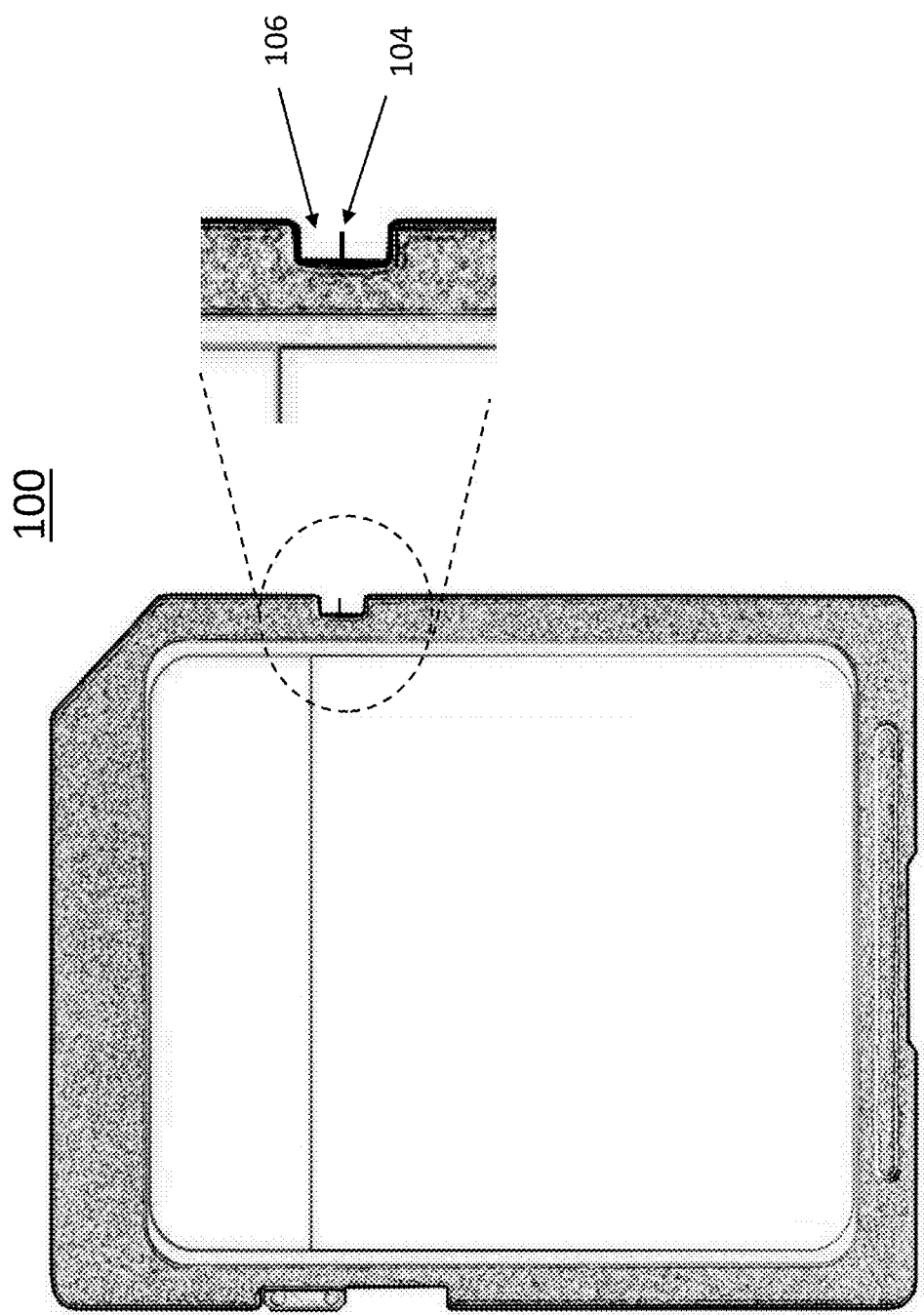
FIG. 31 illustrates an embodiment of a device according to embodiments of the present disclosure in the shape of an SD card.
Figure 32:
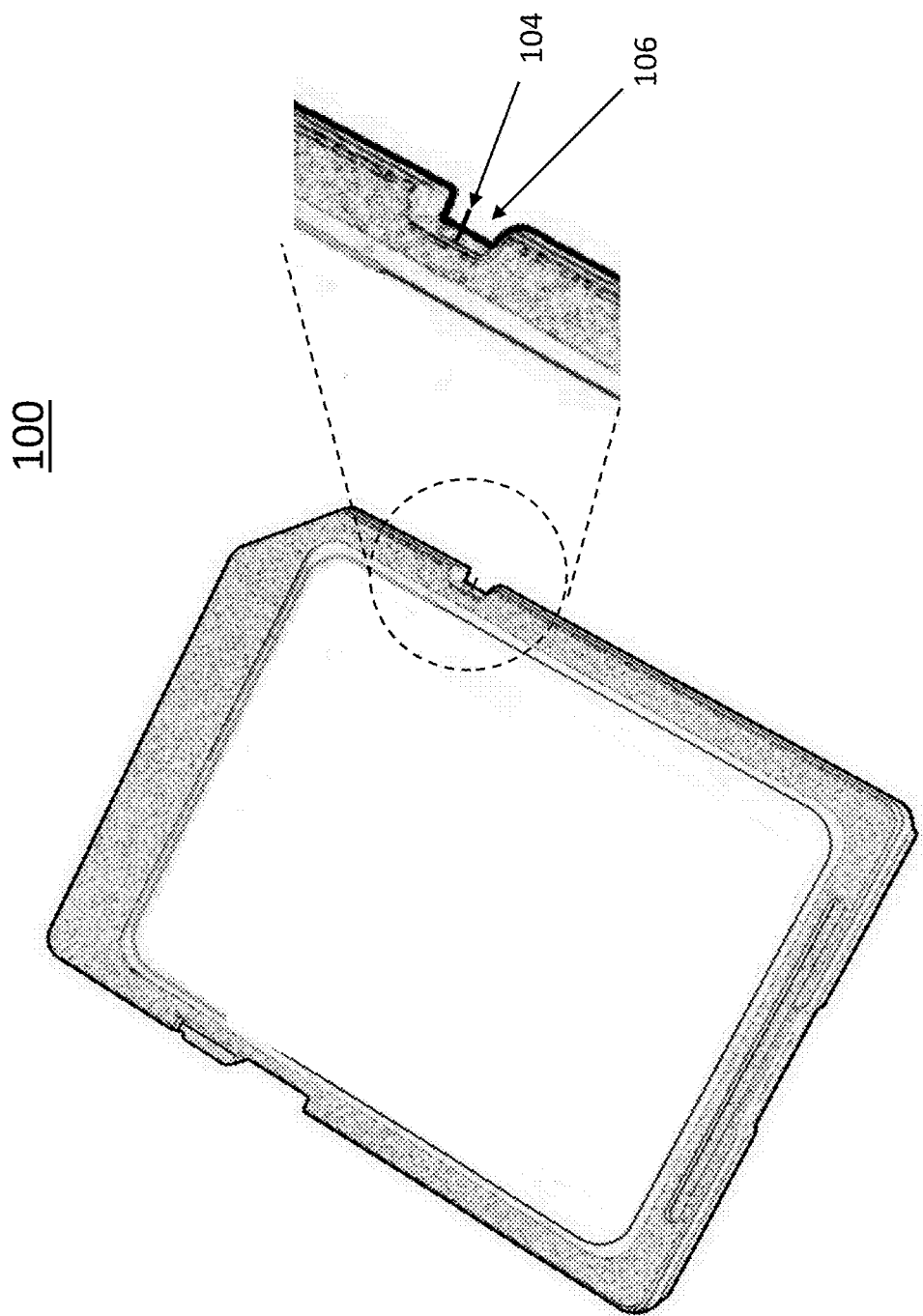
FIG. 32 illustrates another embodiment of a device according to embodiments of the present disclosure in the shape of an SD card.

FIGS. 31 and 32 illustrate an embodiment of the present disclosure wherein the device 100 has the shape of an SD card. Inside the cut-out 106 (which is always present according to SD card standards), a needle 104 is present. At the other side of the SD card, the metal contacts are present and are configured to be electrically connected to the lid 103 to allow read-out of electrical signals from the lid 103, which may be further processed by the device in which the SD card is inserted.

According to embodiments of the present disclosure, the lid 103 or the fluidic substrate 101 may further comprise a compartment for powering the device 100, such as a battery compartment (not illustrated) which is electrically connected to the lid 103.

In a second aspect, embodiments of the present disclosure relate to a method to fabricate a device as disclosed in the first aspect of the present disclosure. One example method comprises providing a fluidic substrate 101, providing a lid 103, and attaching the fluidic substrate 101 to the lid 103 to close the fluidic substrate 101 at least partly. In this example, the fluidic substrate 101 is a silicon fluidic substrate and the lid 103 is CMOS chip. Further, the fluidic substrate 101 may be attached to the lid 103 using a CMOS compatible bonding process.

It is advantageous that the fluidic substrate 101 is bonded to the lid 103 using a CMOS compatible bonding process. In state of the art devices, bonding is performed using high temperature/voltage bonding techniques. These bonding techniques may damage electronic circuitry present in the CMOS chip and/or reagents present in the microfluidic substrate 101. The use of a CMOS compatible bonding enables bonding at lower temperatures/voltages, and therefore preserves the electronic circuitry of the lid 103 and the reagents present in the microfluidic substrate 101. According to embodiments of the present disclosure, the bonding may be performed via a wafer to wafer or die to wafer bonding process, such as direct oxide to oxide bonding or bonding via a patternable polymer. Additionally, it can also be advantageous to be able to perform the bonding at a low temperature in case some reagents are already spotted on one of the substrates during the fabrication flow.

The fluidic substrate 101 may be fabricated using a combination of coarse and fine structures in a single piece of silicon substrate by a combination of two hard masks, protection and de-protection of layers, and etching of coarse and etching of fine structures. The fine structures may be structures configured to enable a controlled capillary suction in the micro-fluidic component 102 of the device 100. The fine structures may comprise micro-pillars 270 and/or other microstructures. The coarse structures may be structures for storing larger volumes of fluids, such as reagent storage 102$b$ for storing reagents, or a wick 102$i$. It is an advantage to use silicon rather than more common microfluidic materials such as glass or polymers since the very high anisotropic etching of silicon results in fine structures with extremely high aspect ratios. The silicon micro-pillars 270 typically have lateral dimensions from 1 um to 20 um with aspect ratios of 20-50. High aspect ratios are advantageous in having a high surface to volume ratio, essential for capillary flow. The high aspect ratio fine structures, combined with the coarse structures facilitate the implementation of more complex capillary fluidic functions in a more compact footprint than is achievable with any other material. More complex functions include separation (e.g. cells from molecules), mixing, valving, thermally controlled reactions, and the like. Moreover, silicon is an inert material with advantages towards implementation of biochemical reactions. The advantage of the extremely compact fully integrated disposable device is facilitated from the advanced use of silicon for both the fluidic substrate and the CMOS lid. The reduced footprint also results in reduced cost of the entire device.

According to embodiments of the present disclosure, providing a fluidic substrate 101 comprises providing a silicon substrate 201, illustrated in FIG. 11, and patterning the silicon substrate to form a micro-fluidic component 102 and a means for providing a fluid sample in the device 100. As discussed herein, the micro-fluidic component 102 is configured to propagate a fluid sample via capillary force through the device 100.

According to embodiments of the present disclosure, providing a fluidic substrate 101 comprises providing a silicon substrate 201, providing an oxide mask 202, and patterning the oxide mask 202 by using a first patternable mask layer 210 so as to create fine structures 203 in the oxide mask 202 (FIG. 12). Further, providing the fluidic substrate includes providing a protection layer 204 to protect the patterned oxide mask, patterning coarse structures in a second patternable mask layer 211 (FIG. 13), etching of the coarse structures 205 in the silicon substrate 201 through the second mask layer 211 (FIG. 14), removing the second mask layer 211 and growing oxide 206 (FIG. 15) for protecting the coarse structures 205, removing the protection layer 204 (FIG. 16) and etching the fine structures 203 using the oxide layer 206 as an etch mask (FIG. 16), and removing the oxide 206 (FIG. 17). The resulting structure is a microfluidic substrate 101 which may be used in a device according to embodiments of the first aspect of the present disclosure.

FIG. 11-17 illustrate how the fluidic substrate 101 may be fabricated. According to embodiments of the present disclosure, the fluidic substrate 101 may be fabricated by performing:

patterning fine structures 203 comprising: providing a silicon substrate 201, providing an oxide mask 202, and patterning the oxide mask 202 to create fine structures 203 in the oxide mask 202;
providing a protection layer 204 to protect the oxide 202;
performing lithography of coarse structures 205;
performing etching of the coarse structures 205;
growing oxide 206 for protecting the coarse structures 205, wherein the protection layer 204 on the fine structures 203 prevents oxide growth;
removing the protection layer 204 and etch the fine structures 203; and
removing the oxide 206.

According to embodiments of the present disclosure, the protection layer 204 may be a nitride layer.

According to embodiments of the present disclosure, providing the CMOS chip 103 comprises providing a silicon substrate 111, fabricating a transistor layer 112 atop the silicon substrate, and providing an interconnection layer 113 atop the transistor layer. The interconnection layer may comprise at least one metal layer. Generally, the CMOS chip 103 is fabricated using standard CMOS process techniques.

Further, on top of standard CMOS process flows, additional components may be deposited or patterned on the interconnection layer 113, such as biocompatible electrodes, a bonding layer, I/O pads, or other components.

According to embodiments of the present disclosure, through-holes 119, 118 may be etched through the fluidic substrate 101 or the CMOS chip 103 to enable fluidic access for applying of reagents to the fluidic substrate 101 or CMOS chip 103. The through-holes in the CMOS chip 103 may be fabricated whilst fabricating silicon I/O interconnections 116 in the CMOS chip 103. The through-holes in the fluidic substrate 101 may be fabricated by first thinning the fluidic substrate 101 and then etching the through-holes.

According to embodiments of the present disclosure, the CMOS chip 103 may be bonded to the fluidic substrate 101 using a die to wafer or wafer to wafer bonding process.

To access electrical signals of the CMOS chip 103, silicon I/O contacts 116 may be provided. According to embodiments of the present disclosure, the contacts may be fabricated by thinning the silicon substrate 111 of the CMOS chip 103 and performing a back side etching on the silicon substrate 111 to gain access to a metal layer of the interconnection layer 113.

Alternatively, a CMOS chip 103 comprising an I/O pad 117 at a first side of the chip 103 may be provided, wherein the first side of the CMOS chip 103 is bonded to the fluidic substrate 101 and wherein the first side of the CMOS chip 103 comprising the I/O pad 117 does not cover the fluidic substrate 101. This is, for example, illustrated in FIG. 22. The I/O pad 117 is accessible when the CMOS chip 103 is bonded to the fluidic substrate 101. The I/O pad 117 may be used as a metal contact on a memory card.

According to embodiments of the present disclosure, the CMOS chip 103 is bonded to the fluidic substrate 101 while aligning at least one electrical component on a first side of a CMOS chip 103 with the micro-fluidic component 102. For example, sensing and actuating electrodes on the first side of the CMOS chip 103 are aligned with a sensing or actuation side in the fluidic substrate 101. This allows direct contact of a fluid sample with electrical components present on the CMOS chip 103 when a fluid sample is present in the device 100.

According to embodiments of the present disclosure, surfaces of the fluidic substrate 101 and the lid 103 are partially or fully coated to modify surface interactions with the fluid sample. The surfaces may be inner surfaces of the micro-fluidic component 102, or a surface of the CMOS chip 103 that is bonded to the fluidic substrate 101, such as those parts of the surface of the CMOS chip 103 that are in contact with a fluid sample present in the micro-fluidic component 102. The coating may be a hydrophilic coating.

The surfaces of the micro-fluidic component 102 and/or the side of the CMOS chip 103 bonded to the fluidic substrate 101 can be made hydrophilic in order to improve the wetting behavior of the surfaces, thereby promoting capillary flow. The surfaces can also be treated in order to avoid absorption or adhesion of biomolecules on the walls. The coating can be done for example by vapor coating with silanes. According to embodiments of the present disclosure the coating may be performed locally on certain parts of the fluidic substrate 101 (e.g. in some micro-fluidic channels) or on certain parts of the CMOS chip 103.

According to embodiments of the present disclosure, at least one through-hole is fabricated in the fluidic substrate 101 by first etching the through-hole and then filling the through-holes with a transparent oxide of polymer.

Embodiments of the present disclosure improve the functionality, portability and manufacturability of compact disposable point-of-care devices. A particular embodiment of the present disclosure is a fully integrated silicon device with a needle or an inlet for the intake of blood or any other body fluid. The device features a capillary fluidic system for the propagation of a fluid sample through the device via capillary action. A capillary pump functioning as the wicking zone of the capillary fluidic system may be used to help propagate the fluid sample in the device. A sensor chip reading out signals produced by biochemical sensing reactions inside the capillary system may be used to add bio-sensing functionality to the device. Further, the device may feature a data communication interface for sending data to a personal computer, a computing unit, smartphone or any other wireless communication device. The device may function as a stand-alone system wherein a power interface such as a battery powers electronic circuitry such as a micro-chip in the device. Alternatively, the device may be powered via a communication port of the device.

The device may further comprise fluidic manipulation structures including filtering, mixing, and valves structures. A protection structure with a cut off zone to protect and prevent breaking the needle before usage may be present to avoiding contamination before usage. Structures such as electrically controllable fluidic manipulation structures including electrowetting, electro and dielectrophoretic manipulation may be present to interact with a fluid sample in the device. Electronic controllable heaters may be present for accurately controlling the temperature of the chip or for thermal cycling purposes.

Another example embodiment of the present disclosure includes an elegant, low cost and compact manner to fabricate all of the above functions by providing a silicon substrate which may comprise lithographically defined channels, micro pillars and microstructures of various shapes fabricated by deep Reactive Ion Etching and designed to function as a capillary fluidic platform. The silicon substrate may have a provision for making a needle and a cut off zone for protecting the needle. The silicon substrate can have different etch depths allowing for precise control over the volume and capillary flow of a fluid sample in the device. The silicon substrate may be closed by a CMOS substrate (such as lid 103) comprising CMOS electronics containing a transistor layer. The electronics may be designed to provide functionality including sensing, actuating, signaling, data processing, and data communication, and therefore replaces the point-of-care instrument. Some of the electrodes may be in direct contact with the fluid, and these electrodes may be protected in a fluid compatible manner. The silicon substrate may be closed by the CMOS substrate by bonding both substrates in a leakage free and biocompatible manner. This can be done via a wafer to wafer or die to wafer bonding process such as bonding via a patternable polymer. The inner silicon substrate surfaces which may be in contact with the body fluids may feature a hydrophilic layer via coating of the inner channels. Additionally, through wafer holes may be fabricated in the silicon substrate for supplying reagents after the device has been bonded. For each analysis, different reagents can be supplied. As an advantage, the same device becomes configurable for different diseases by simply adding reagents through the through-holes in the last production step, for example. The device may be manufactured using CMOS compatible processing steps which lower production cost and enable the device to be used as disposable device.

Further, the device may comprise components to enable interfacing with standard user interfaces. For example, the use of such a device as a smartcard in wireless communication devices inserted in slots typically foreseen for smartcards. For example, the use of such a device together with a compact and cheap battery and low cost communication device (e.g. Bluetooth, NFC). For example, the use of such a device together with a wired communication interface (e.g. USB)

Embodiments of the present disclosure may be used to detect DNA/RNA from body fluids and perform an analysis to detect: mutations (ancestry, drug dosing, and disease predisposition), miRNA (marker for cancer and other diseases), pathogen DNA/RNA (infectious diseases such as HepC, HIV, etc.), and microbiome DNA. Further, the device may be used to detect proteins such as biomarkers for a specific disease (cancer, Alzheimer's, infectious diseases, heart disease, cancer etc.). Further, the device may be used to detect small molecules and metabolites to reveal metabolic information (e.g., cholesterol). Further, the device may be used to detect biomarkers from exosomes. Further the device may be used to perform microscopy to perform a blood count, analyze cells present in the blood (e.g. circulating tumour cells), identify infectious agents (e.g. malaria), and to detect blood disorders (e.g. sickle cell anemia).

The invention claimed is:

1. A device for analyzing a fluid sample, the device comprising:
    a fluidic substrate comprising:
        a micro-fluidic component embedded in the fluidic substrate and configured to propagate a fluid sample via capillary force through the micro-fluidic component, and
        a means for providing a fluid sample connected to the micro-fluidic component; and
    a lid attached to the fluidic substrate, at least partly covering the fluidic substrate, and at least partly closing the micro-fluidic component,
    wherein the fluidic substrate is a silicon fluidic substrate, and wherein the lid is a Complimentary Metal-Oxide Semiconductor (CMOS) chip, wherein the CMOS chip includes at least one electrical component, and wherein the at least one electrical component is in direct contact with the fluid sample when the fluid sample is present in the device.

2. The device according to claim 1, wherein the lid comprises a transistor layer electrically connected to the at least one electrical component, and wherein the at least one electrical component includes at least one of the following: biosensing circuitry, an electrode for sensing purposes, an electrode for fluid manipulation purposes, circuitry for data communication purposes, circuitry for wireless data communication purposes, a temperature sensor, a heater electrode for temperature control, or a fluid sensor and an electrode for fluidic viscosity control.

3. The device according to claim 1, wherein the means for providing a fluid sample is an integrated needle fabricated from silicon and comprising an inner fluidic channel connected to the micro-fluidic component, and wherein the needle is a protruding portion of the fluidic substrate and is positioned to penetrate skin tissue when pressed against the skin tissue.

4. The device according to claim 3, wherein the fluidic substrate comprises a cut-out, and wherein the needle is positioned in the cut-out.

5. The device according to claim 3, wherein the fluidic substrate comprises a protection structure for protecting the needle, and wherein the protection structure is removably attached to the fluidic substrate.

6. The device according to claim 1, wherein the fluidic substrate further comprises at least one optical waveguide to allow optical excitation and sensing of the fluid sample when present in the device.

7. The device according to claim 1, wherein at least one of the fluidic substrate or the lid comprises at least one through-hole for application of a biochemical reagent to at least one region of the micro-fluidic component or to at least one region of the lid.

8. The device according to claim 1, wherein the lid is bonded to the fluidic substrate using a lithographically patterned polymer.

9. The device according to claim 1, further comprising metal contacts electrically connected to the lid for read-out of electrical signals from the lid.

10. The device according to claim 1, wherein at least part of one or more of the fluidic substrate or the lid is fabricated from a transparent material to allow optical inspection of a fluid sample when the fluid sample is present in the micro-fluidic component.

11. The device according to claim 1, wherein the device is configured to allow insertion into a mobile communication device.

12. The device according to claim 1, wherein the micro-fluidic component further includes micro-pillars arranged to create the capillary force that propagates the fluid sample through the micro-fluidic component.

13. The device according to claim 12, wherein the micro-pillars are arranged to create the capillary force by varying one or more of distances between micro-pillars, dimensions of the micro-pillars, or shapes of the micro-pillars.

14. A device for analyzing a fluid sample, the device comprising:

a fluidic substrate comprising a micro-fluidic component embedded in the fluidic substrate and configured to propagate a fluid sample via capillary force through the micro-fluidic component, wherein the fluidic substrate is a silicon fluidic substrate; and a CMOS chip attached to the silicon fluidic substrate, at least partly covering the fluidic substrate, and at least partly closing the micro-fluidic component, wherein the CMOS chip includes at least one electrical component, and wherein the at least one electrical component is in direct contact with the fluid sample when the fluid sample is present in the device.

15. A method for fabricating a device for analyzing a fluid sample, the method comprising:
    providing a fluidic substrate comprising a micro-fluidic component embedded in the fluidic substrate and configured to propagate a fluid sample via capillary force through the micro-fluidic component, and a means for providing a fluid sample connected to the micro-fluidic component;
    providing a lid; and
    attaching the fluidic substrate to the lid to close the fluidic substrate at least partly,
    wherein the fluidic substrate is a silicon fluidic substrate and the lid is CMOS chip,
    wherein the CMOS chip includes at least one electrical component, and wherein the at least one electrical component is in direct contact with the fluid sample when the fluid sample is present in the device,
    and wherein the fluidic substrate is attached to the lid using a CMOS compatible bonding process.

16. The method according to claim 15, wherein providing the fluidic substrate comprises:
    providing a silicon substrate, providing an oxide mask, and patterning the oxide mask to create fine structures in the oxide mask;
    providing a protection layer to protect the oxide mask;
    patterning coarse structures;
    etching of the coarse structures;
    growing oxide for protecting the coarse structures;
    removing the protection layer;
    etching the fine structures; and
    removing the oxide.

17. The method according to claim 15, wherein surfaces of the fluidic substrate and the lid are partially or fully coated to modify surface interactions of the substrate with the fluid sample.

18. Use of the device according to claim 1 to perform microscopy.

* * * * *